United States Patent
Zimmerman et al.

(10) Patent No.: US 6,564,154 B1
(45) Date of Patent: May 13, 2003

(54) MONITORING SYSTEM

(75) Inventors: Lynn A. Zimmerman, Rockford, MI (US); Ronald J. Kerkstra, Jr., Allegan Grand Haven, MI (US); Patricia Robin Hood, Grand Haven, MI (US); Kenneth L. Trumble, Jenison, MI (US); James M. Kerkstra, Kentwood, MI (US); Edward C. Smit, Jr., Lowell, MI (US); Patrick J. Fingleton, Grand Rapids, MI (US)

(73) Assignee: Steelcase Development Corporation, Caledonia, MI (US)

( * ) Notice: Subject to any disclaimer, the term of this patent is extended or adjusted under 35 U.S.C. 154(b) by 96 days.

(21) Appl. No.: 09/724,796

(22) Filed: Nov. 28, 2000

(51) Int. Cl.[7] .............................................. G01N 31/00
(52) U.S. Cl. .......................... 702/24; 702/24; 702/50; 702/122; 702/176; 73/1.02; 73/1.16; 73/19.02; 700/9; 700/17; 700/83; 700/266; 427/331; 427/335; 427/337
(58) Field of Search ............................ 702/1, 5, 12, 13, 702/22, 23, 24, 47, 50, 52–53, 122–124, 126, 176, 188, 189; 700/9, 11–12, 17–19, 23, 28, 67, 68, 75, 83, 84, 91, 171, 174, 266, FOR 102; 73/1.02, 1.05, 1.16, 1.35, 1.36, 19.02, 23.35, 23.42; 427/331, 335, 336, 337, 349, FOR 103, FOR 104

(56) References Cited

U.S. PATENT DOCUMENTS

| | | | |
|---|---|---|---|
| 4,562,088 A | 12/1985 | Navarro | 427/8 |
| 5,165,969 A | 11/1992 | Barlett et al. | 427/421 |
| 5,225,239 A | 7/1993 | Ostin | 427/8 |
| 5,443,642 A | 8/1995 | Bienduga | 118/688 |
| 5,668,735 A * | 9/1997 | Dominguez et al. | 364/497 |
| 5,831,855 A | 11/1998 | Kinsman | 364/468.13 |
| 5,832,411 A | 11/1998 | Schatzmann et al. | 702/23 |
| 5,932,011 A | 8/1999 | Noakes et al. | 118/629 |
| 5,976,612 A | 11/1999 | Tardoni | 427/8 |
| 6,023,644 A | 2/2000 | Kinsman | 700/230 |
| 6,027,759 A | 2/2000 | Kwok et al. | 427/8 |
| 6,045,056 A | 4/2000 | Tardoni | 239/8 |
| 6,405,135 B1 * | 6/2002 | Adriany et al. | 702/5 |

OTHER PUBLICATIONS

IT Corporation, "Steelcase Trigger Time Database Documentation," bearing a designation of "Oct. 15, 1997" (40 sheets).

Oracle Corporation, "Oracle7 Server Application Developer's Guide—Maintaining Data Integrity," Bearing a designation of "Jan. 8, 2001" (21 sheets).

Jennifer M. Granholm, "For Immediate Release," bearing a designation of "Aug. 16, 2000" (2 sheets).

The Grand Rapids Press, "Steelcase will pay $346,000 penalty," bearing a designation of "Aug. 17, 2000" (2 sheets).

* cited by examiner

Primary Examiner—Marc S. Hoff
Assistant Examiner—Elias Desta
(74) Attorney, Agent, or Firm—Foley & Lardner

(57) ABSTRACT

A system for monitoring the emission of VOCs in a workstation is disclosed including a sensor to obtain a signal representative of the amount of coating discharged in the workstation, a database for storing data values representative of the signal, a network configured for allowing access to the database and at least one computing device for access to the database over the network and providing a user interface for presenting information representative of at least a portion of the data values. A method for monitoring the emission of VOCs in a workstation is disclosed.

89 Claims, 44 Drawing Sheets

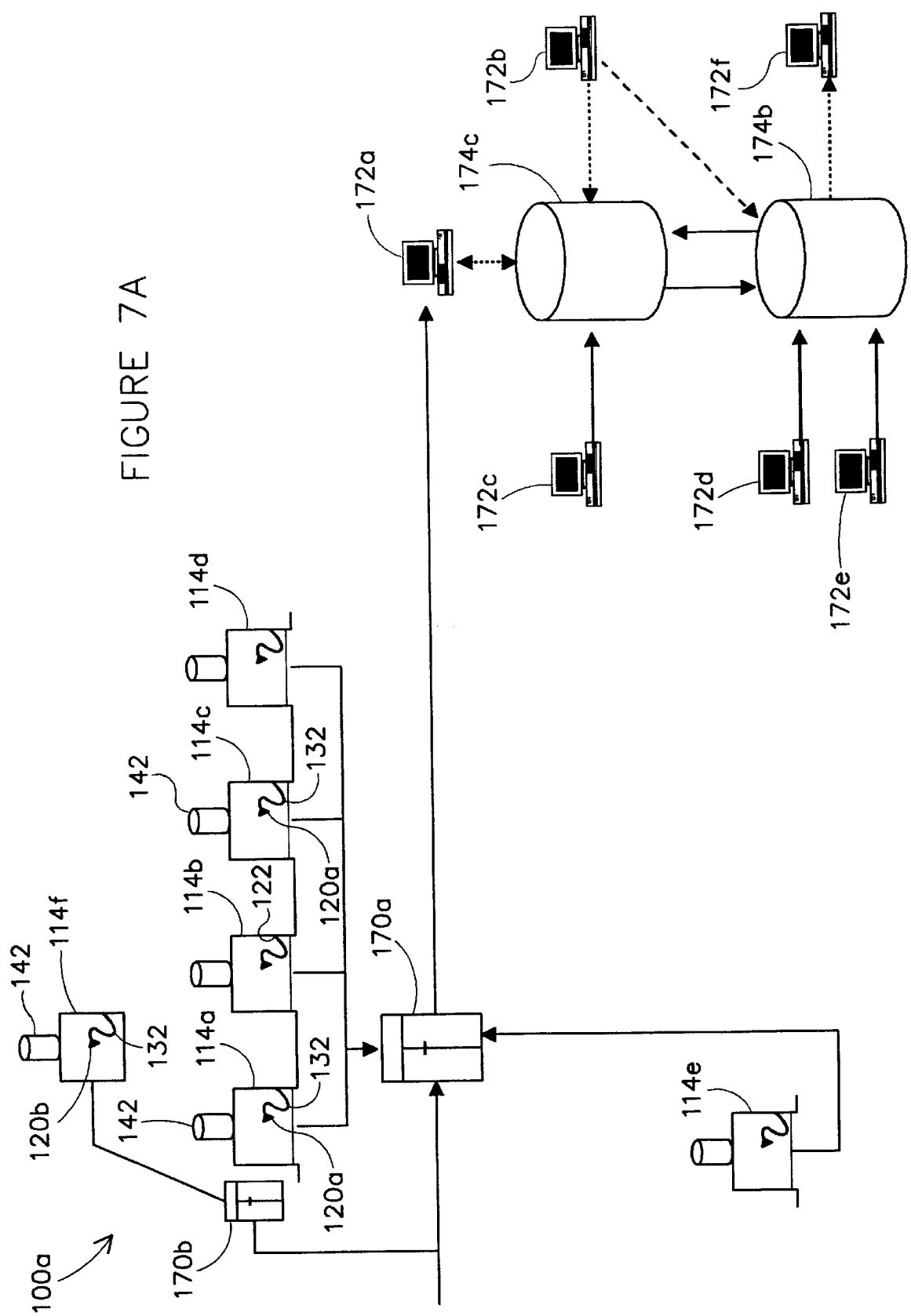

FIGURE 9B

| CONTACT | | |
|---|---|---|
| * | A | LAST NAME |
| * | A | FIRS NAME |
|  | A | ORGANIZATIO NAME |
|  | A | LOCATION |
| # | 789 | ID |
| * | A | WORKPHONE |
|  | A | PAGE |
|  | A | FAX NUMBER |

*=NOT NULL, #=PRIMARY, O=OPTIONAL,
A=ALPHANUMERIC, 789=NUMERIC

FIGURE 9C

| BATCH CONTENT 1 | | |
|---|---|---|
|  | 789 | PLANT ID |
| O | A | COLOR |
| O | A | BATCH |
| O | 789 | VOC RAW |
| O | 789 | SUM OF RAW PAINT |
| O | 789 | VOC CONTENT |
| O | 789 | SUM OF REDUCER ADDED |

*=NOT NULL, #=PRIMARY, O=OPTIONAL,
A=ALPHANUMERIC, 789=NUMERIC

FIGURE 9D

| BATCH CONTENT 3 | | |
|---|---|---|
| O | 789 | PLANT ID |
| O | A | COLOR |
| O | A | BATCH |
| O | 789 | VOC RAW |
| O | 789 | SUM OF RAW PAINT |
| O | 789 | VOC CONTENT |
| O | 789 | SUM OF REDUCER ADDED |

*=NOT NULL, #=PRIMARY, O=OPTIONAL,
A=ALPHANUMERIC, 789=NUMERIC

FIGURE 9E

| BATCH CONTENT 4 | | |
|---|---|---|
| * | A | COLOR |
| O | 789 | MAX VOC RAV |

*=NOT NULL, #=PRIMARY, O=OPTIONAL,
A=ALPHANUMERIC, 789=NUMERIC

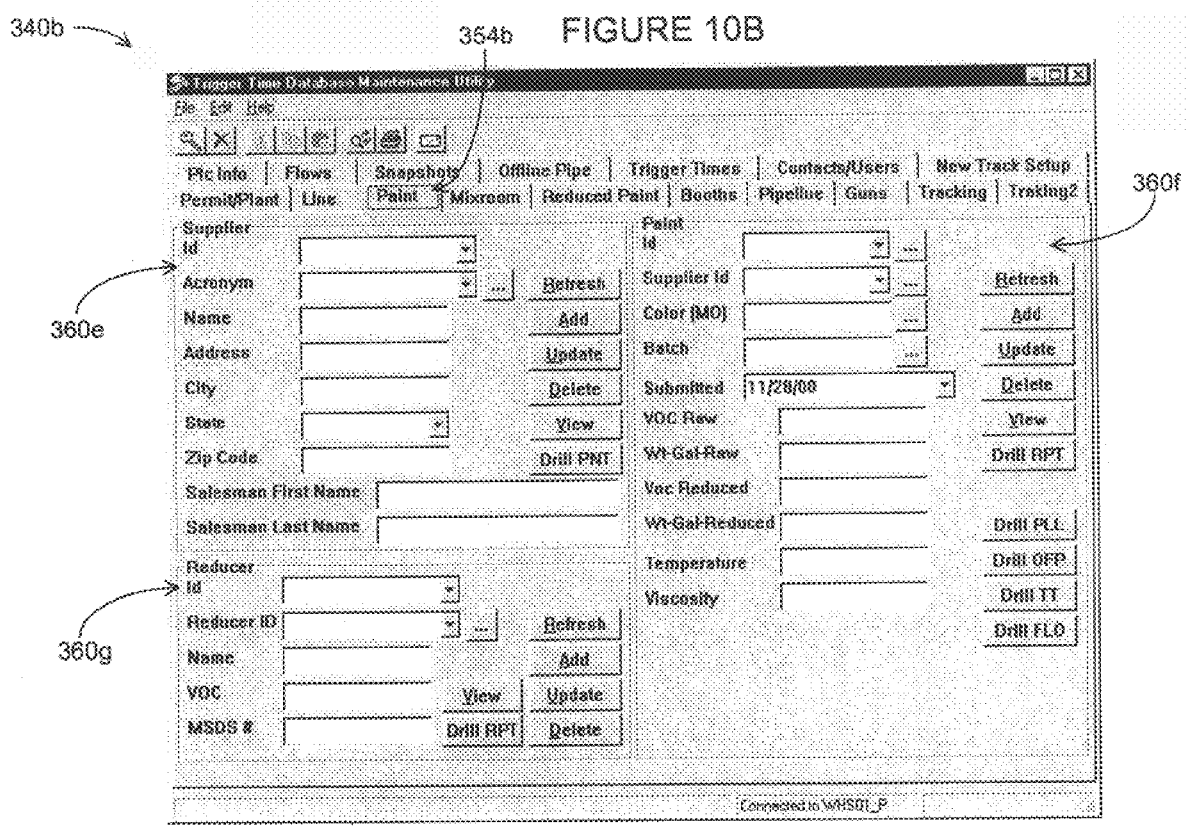

| Name | Active | Color | Batch | Name | Active | Color | Batch |
|---|---|---|---|---|---|---|---|
| 01 | no | 4788 | | 15 | no | 4690 | |
| 02 | no | 4762 | | 16 | no | 4781 | |
| 03 | Yes | 0835 | | 17 | no | 4792 | |
| 04 | no | 4684 | | 18 | no | 4607 | |
| 05 | no | 4791 | | 19 | no | 3939 | |
| 06 | no | 4606 | | 20 | no | 4719 | |
| 07 | no | 4773 | | 21 | no | 4775 | |
| 08 | no | 4790 | | 22 | no | 4794 | |
| 09 | no | 4601 | | 23 | no | 4682 | |
| 10 | no | 4658 | | 24 | no | 4763 | |
| 11 | no | 4793 | | 25 | no | 4718 | |
| 12 | no | 4795 | | Bucket1 | no | 4654 | |
| 13 | no | 4761 | | Bucket2 | no | 4897 | |
| 14 | no | 4686 | | | | | |

VOC EMISSIONS REPORT
Paint Sprayed (No flush solvent included)
From 9/4/00 To 9/10/00

Plant Name:
  Metal Line 1 Grand Total Sprayed:
  Metal Line 1 Grand Total Uncontrolled VOC Emitted:
  Metal Line 1 Grand Total Controlled VOC:

Plant Name:                          Line Name:
  Booth 3 Total Paint Sprayed:
  Booth 3 Uncontrolled VOC Emitted:
  Booth 3 Total Controlled VOC:

| Date | Paint Sprayed (gallons) | Uncontrolled VOC Emitted (lbs) | Capture Efficiency (%) | Destruction Efficiency (%) | Overall Efficiency (%) | Controlled VOC (lbs) |
|---|---|---|---|---|---|---|
| 09/05/2000 | | | | | | |
| 09/07/2000 | | | | | | |

FIGURE 14A

PPGS
(Pounds of VOC per Gallon of Coating Solids as Applied)
From 8/26/00 To 9/10/00

Plant Name:
- Hard Line Total Paint Sprayed: _____ (gallons)
- Hard Line Total Uncontrolled VOC Emitted: _____ (lbs)
- Hard Line Total Coating Solids: _____ (gallons)

| Date | Paint Sprayed (gallons) | Uncontrolled VOC Emitted (lbs) | Coating Solids (gallons) | Volume Wieghted Average Transfer Efficiency (%) | Capture Efficiency (%) | Destruction Efficiency (%) | Overall Control Eff. (%) | Uncontrolled VOC Applied Solids (lbs / gallon) | Controlled VOC Applied Solids (lbs / gallon) |
|---|---|---|---|---|---|---|---|---|---|
| 8/26/2000 | | | | | | | | | |
| 8/27/2000 | | | | | | | | | |
| 8/28/2000 | | | | | | | | | |
| 8/29/2000 | | | | | | | | | |
| 8/30/2000 | | | | | | | | | |
| 8/31/2000 | | | | | | | | | |
| 8/01/2000 | | | | | | | | | |

FIGURE 14B

PPGS using Flow Meters
(Pounds of VOC per Gallon of Coating Solids as Applied)
From 9/1/00 To 9/10/00

Plant Name:
Line Name:

| Date | Paint Sprayed (gallons) | Uncontrolled VOC Emitted (lbs) | Coating Solids (gallons) | Volume Weighted Average Transfer Efficiency (%) | Capture Efficiency (%) | Destruction Efficiency (%) | Overall Control Eff. (%) | Uncontrolled VOC Applied Solids (lbs / gallon) | Controlled VOC Applied Solids (lbs / gallon) |
|---|---|---|---|---|---|---|---|---|---|
| 9/01/2000 | | | | | | | | | |
| 9/02/2000 | | | | | | | | | |
| 9/03/2000 | | | | | | | | | |
| 9/04/2000 | | | | | | | | | |
| 9/05/2000 | | | | | | | | | |
| 9/06/2000 | | | | | | | | | |
| 9/07/2000 | | | | | | | | | |

FIGURE 14C

SURFACE COATING USAGE
From 9/4/00 To 9/10/00

Line Name:

| Date | Color | Batch | Trigger Time (seconds) | Total Paint Sprayed (gallons) | Reduced Raw Paint (gallons) | Reducer Added (gallons) | Raw Paint Sprayed (gallons) | Reducer Sprayed (gallons) |
|---|---|---|---|---|---|---|---|---|
| 9/04/2000 | 4761 | | | | | | | |
| 9/05/2000 | 4779 | | | | | | | |
| 9/05/2000 | 4687 | | | | | | | |
| 9/05/2000 | 4777 | | | | | | | |
| 9/05/2000 | 4654 | | | | | | | |
| 9/05/2000 | 4776 | | | | | | | |
| 9/05/2000 | 4784 | | | | | | | |

FIGURE 14D

FLUSH SOLVENT USAGE
From 8/1/00 To 8/31/00

| Furniture |
| --- |

| Line |
| --- |

| Trigger Time (seconds) | Solvent Used (gallons) | VOCs @ 7.25 lbs. VOC/gal (pounds) |
| --- | --- | --- |
|  |  |  |

| Line |
| --- |

| Trigger Time (seconds) | Solvent Used (gallons) | VOCs @ 7.25 lbs. VOC/gal (pounds) |
| --- | --- | --- |
|  |  |  |

FIGURE 14E

Line Operating Times

8/1/2000

| Line | Time (hours) | |
|---|---|---|
| Hand Line | Hand Line | |
| Liquid Line | Liquid Line | |

8/2/2000

| Line | Time (hours) | |
|---|---|---|
| Hand Line | Hand Line | |
| Liquid Line | Liquid Line | |

8/3/2000

| Line | Time (hours) | |
|---|---|---|
| Hand Line | Hand Line | |
| Liquid Line | Liquid Line | |

8/4/2000

| Line | Time (hours) | |
|---|---|---|
| Hand Line | Hand Line | |
| Liquid Line | Liquid Line | |

FIGURE 14F

PURGE SECONDS

Plant

| Month | Year | Evt Id | Event Number | Line Id | Booth Number | Gun Id | Trigger Number |
|---|---|---|---|---|---|---|---|
| 8 | 2000 | 2 | 2 | Mtl1 | 3 | 62 | |
| 8 | 2000 | 2 | 2 | Mtl1 | 5 | 64 | |
| 8 | 2000 | 2 | 2 | Mtl1 | 5 | 64 | |
| 8 | 2000 | 2 | 2 | Mtl1 | 5 | 65 | |
| 8 | 2000 | 2 | 2 | Mtl1 | 5 | 65 | |
| 8 | 2000 | 2 | 2 | Mtl1 | 5 | 65 | |
| 8 | 2000 | 2 | 2 | Mtl1 | 5 | 65 | |
| 8 | 2000 | 2 | 2 | Mtl1 | 5 | 65 | |
| 8 | 2000 | 2 | 2 | Mtl1 | 6 | 66 | |
| 8 | 2000 | 2 | 2 | Mtl1 | 6 | 66 | |
| 8 | 2000 | 2 | 2 | Mtl1 | 6 | 66 | |
| 8 | 2000 | 2 | 2 | Mtl1 | 6 | 66 | |
| 8 | 2000 | 2 | 2 | Mtl1 | 6 | 66 | |
| 8 | 2000 | 2 | 2 | Mtl1 | 6 | 130 | |
| 8 | 2000 | 2 | 2 | Mtl1 | 8 | 135 | |
| 8 | 2000 | 2 | 2 | Pwd2 | 6 | 131 | |
| 8 | 2000 | 2 | 2 | Pwd2 | 6 | 132 | |
| 8 | 2000 | 2 | 2 | Pwd2 | 6 | 133 | |

FIGURE 14G

MONITORING SYSTEM

FIELD OF THE INVENTION

The present invention relates to a monitoring system. More specifically, the present invention relates to a monitoring system for monitoring VOC emissions in an enterprise.

BACKGROUND

Volatile organic compounds (VOCs) released into the atmosphere are believed to contribute to the formation of ground-level ozone or smog. Sewage treatment facilities, electronics manufacturers, chemical manufacturers, woodworking industries, baking facilities, dry cleaners, petroleum refineries, printers and painting operations are believed to release VOCs into the atmosphere.

VOC emissions from painting operations may be subject to federal, state and/or local permit limits. Some permit limits regulate specific painting line emissions, and other permit limits regulate an entire plant. In order to comply with these limits, operators of painting operations report emissions and deviations in operating parameters on a regular or periodic basis (e.g., quarterly).

It is generally known to limit the use of VOC emitting paints by substitution of powder coatings, which may not emit VOCs. However, such powder coatings are disadvantageous because they are relatively expensive and create a relatively large amount of waste materials. Some have attempted to limit the number of VOC emissions by monitoring total VOC emissions from painting operations and recording information on a computer. However, such known monitoring is disadvantageous because it does not necessarily fully allow networked access of the information across the business enterprise, could be bypassed by a paint spray operator and does not provide VOC emission data on demand.

Accordingly, it would be advantageous to provide a VOC monitoring system for acquiring data and performing calculations to provide essentially real time customizable reports that indicate regulatory compliance for the application of spray coatings. It would also be advantageous to provide a VOC monitoring system that keeps and maintains adequate records to meet state and federal limits for VOC emissions produced by the surface coating of metal furniture. It would also be advantageous to provide a VOC monitoring system that facilitates overall monitoring of the manufacturing process for the application of spray coatings. It would also be advantageous to provide a VOC monitoring system that reduces the likelihood of user error, facilitates accurate recording of data, restricts access to the data, provides data integrity and provides a vehicle to correct data errors. It would also be advantageous to provide a customizable or adaptable user interface adaptable to variations or changes in a spray coating. It would also be desirable to provide for a monitoring system having one or more of these or other advantageous features.

SUMMARY

The present invention relates to a system for monitoring the emission of VOCs in a workstation including a sensor to obtain a signal representative of the amount of coating discharged in the workstation, a database for storing data values representative of the signal, a network configured for allowing access to the database and at least one computing device for access to the database over the network and providing a user interface for presenting information representative of at least a portion of the data values.

The present invention further relates to a system for monitoring the emission of VOCs in a workstation in a work environment accessible by users including a sensor to obtain a signal representative of the amount of a coating discharged in the workstation, a local database configured to store data values representative of the coating, a corporate database configured to retrieve the data values from the local database and a network configured to permit manipulation of the data values in the corporate database.

The present invention further relates to a method of monitoring the emission of VOCs in a workstation including measuring a signal representative of the amount of a coating discharged in the workstation, storing a data value representative of the amount of a coating discharged in the workstation in a database, inputting data values representative of the coating in the database and representative of the data values.

DESCRIPTION OF THE FIGURES

FIG. 7A is a schematic diagram of a monitoring system for monitoring VOC emissions according to a preferred embodiment.

FIG. 9B is a schematic diagram of a database table showing contact information according to a preferred embodiment.

FIG. 9C is a schematic diagram of a database view showing batch content information according to a preferred embodiment.

FIG. 9D is another schematic diagram of a database view showing batch content information according to a preferred embodiment.

FIG. 9E is another schematic diagram of a database view showing batch content information according to a preferred embodiment.

FIG. 10B is a user interface showing paint information and intended for interaction with an operator via a computing device according to an exemplary embodiment.

FIG. 11A is a user interface showing pipeline color and batch information and intended for interaction with an operator via a computing device according to an exemplary embodiment.

FIG. 11C is a user interface showing pipeline color change information and intended for interaction with an operator via a computing device according to an exemplary embodiment.

FIG. 14A is a report showing pounds of VOC emissions according to an exemplary embodiment.

FIG. 14B is a report showing pounds of VOC per gallon of coating solids as applied according to an exemplary embodiment.

FIG. 14C is a report showing pounds of VOC per gallon of coating solids as applied using flow meters according to an exemplary embodiment.

FIG. 14D is a report showing surface coating usage according to an exemplary embodiment.

FIG. 14E is a report showing pounds of flush solvent usage according to an exemplary embodiment.

FIG. 14F is a report showing line operating time according to an exemplary embodiment.

FIG. 14G is a report showing flush time according to an exemplary embodiment.

DETAILED DESCRIPTION OF PREFERRED AND OTHER EXEMPLARY EMBODIMENTS

Figure 1:
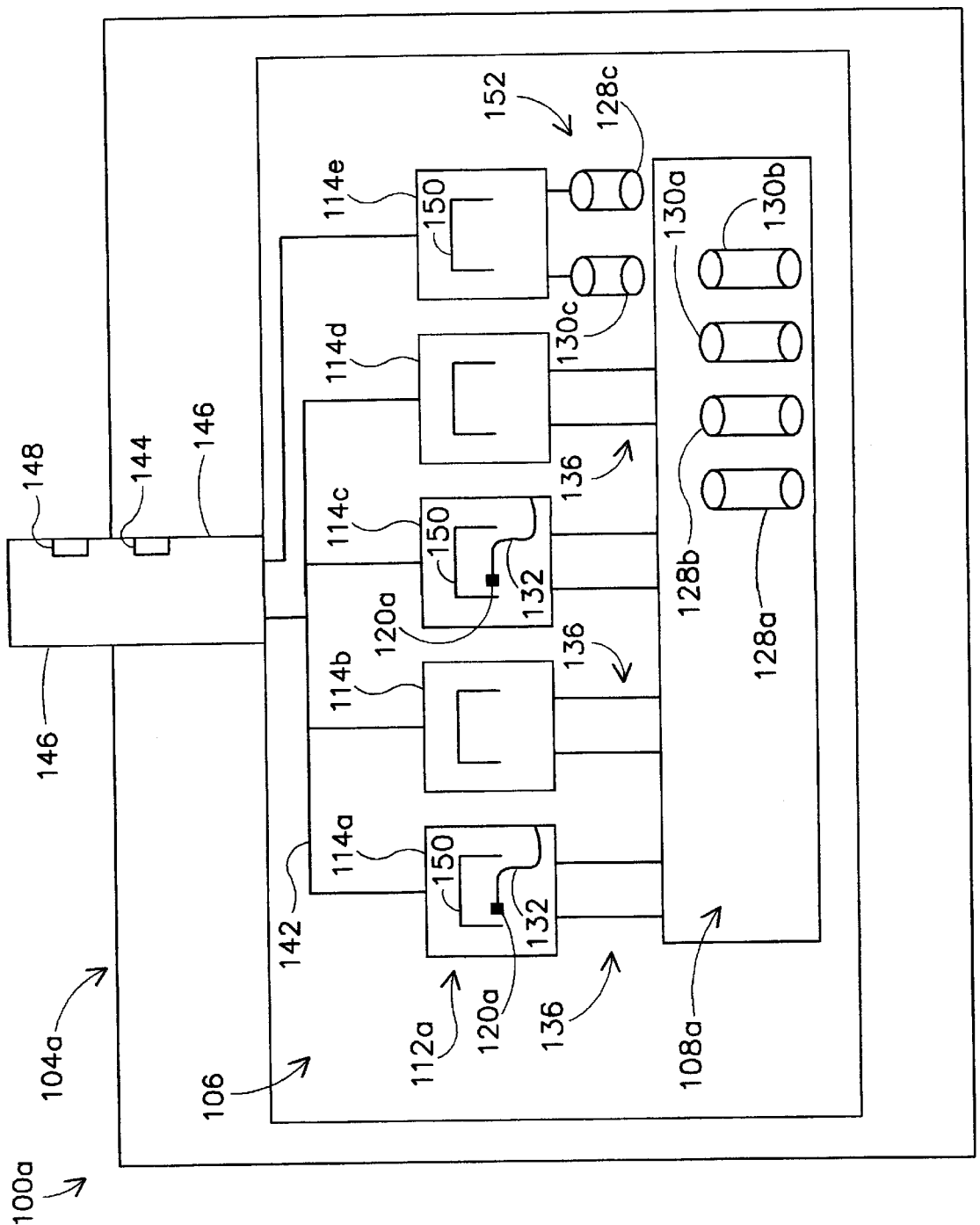
FIG. 1 is a schematic diagram of a monitoring system for monitoring VOC emissions according to an exemplary embodiment.

A monitoring system 100a for monitoring VOC emissions is shown in FIG. 1. Monitoring system 100a is shown in a work environment or manufacturing facility (shown as a plant 104a). Plant 104a is used as a facility for applying a coating such as paint to an unfinished workpiece or article of furniture having a metal part or painting surface. The workpiece is brought to a coating or paint room 106 for application of the coating along a coating line 112a. (The workpiece may be provided as a series of parts on an automated belt or conveyor.)

Line 112a includes an individual booth or workstation (shown as workstations 114a through 114d) for application of the coating on the workpiece. Each workstation has an applicator or gun 120a for spraying, discharging, delivering or applying the coating to the workpiece. According to an alternative embodiment, the workstation may include multiple guns for spraying different surfaces (e.g., top, bottom, etc.) of the workpiece in three dimensions.

A mix room 108a serves as a primary source of the coating for workstations 114a through 114d, and a location for reduction of the coating. The coating includes raw paint (e.g., about 35% by total weight volume) and a reducer or solvent (e.g., about 65% by total weight volume). The raw paint includes solids such as pigments, binders, emulsifiers, resins, etc. The raw paint is "cut," diluted or carried with the solvent. The components of the coating are shown stored separately (i.e., in individual containers or tanks) in FIG. 1. As shown in FIG. 1, the raw coating component of the coating is stored in a raw coating source 128a and a raw coating source 128b (e.g., a container), and the solvent component of the coating is stored in a solvent source 130a and a solvent source 130b (e.g., a container, tank, drum, etc.). Suitable solvents that are VOCs include xylene, ethyl benzene, n-butyl acetate, butyl carbitol acetate (BCA), petroleum hydrocarbons, naphthalene, 1-2-4-trimethyl benzene, acetone, etc., and combinations thereof.

A pipe 136 channels the coating from mix room 108a to workstations 114a through 114d. Raw coating source 128a is mixed with solvent source 130a and provided to workstation 114a by pipe 136. Workstation 114e (an "offline" workstation) is not necessarily supplied with components for the coating by mix room 108a, and is provided with the coating by a raw coating source 128c mixed with a solvent source 130c. The mixed components for the coating are provided to workstation 114e by a pipe 152.

The components of the coating may include volatile organic compounds (VOCs). VOC emissions are believed to occur from the discharge and curing of VOC present in the coating during application. Both the raw coating and the solvent of the coating include VOCs. Specifically, VOCs may be released as these components "volatilize" with air. (The VOCs are not necessarily released while the coating is contained or channeled in pipes 132, 136 and 152.)

Any coating discharged from gun 120a that is not applied directly to the workpiece is collected in a recovery system (shown as a hood 150) for subsequent recycling or destruction. According to an alternative embodiment, an operator may be separated from the workpiece by a partition, barrier, screen, etc. Materials in the coating that "volatilize" or evaporate are routed through a vent 142 to an outlet or discharge (shown as a stack 146) of plant 104a. The volatilized coating is captured, stored, recycled or destroyed by an add-on emission control device (shown as an incinerator or thermal oxidizer 148). The volatilized coating is then discharged to the atmosphere through stack 146 as uncontrolled VOC. According to an alternative embodiment as shown in FIG. 1, testing equipment 144 is provided in stack 146 to measure particulate emissions.

Figure 2:
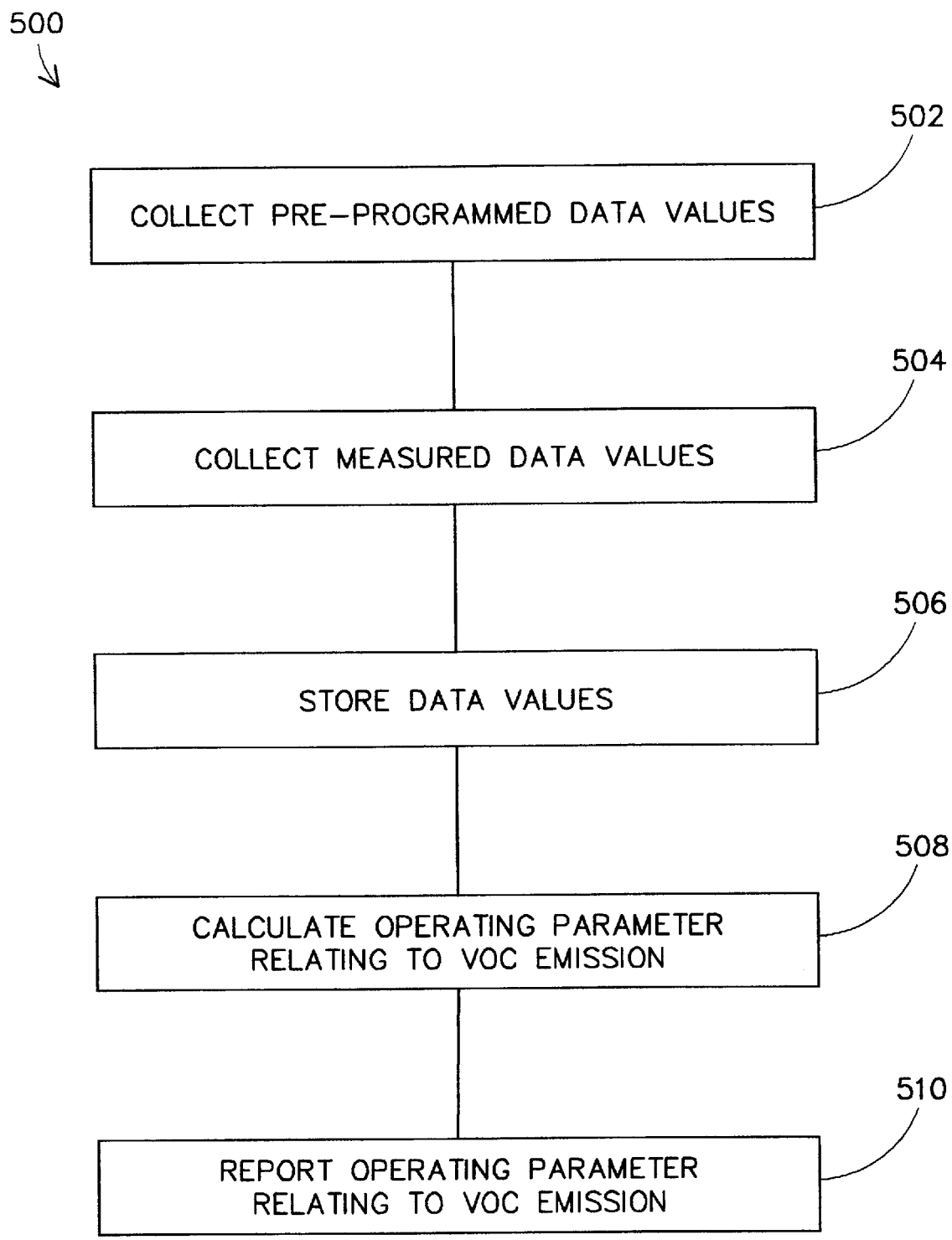
FIG. 2 is a block diagram of a method of monitoring VOC emissions according to an exemplary embodiment.

FIG. 2 shows a method 500 of monitoring the application of spray coatings. Method 500 is implemented over a network of computing devices to track the amount (e.g. volume) of VOC emissions during application of the coating.

Figure 3:
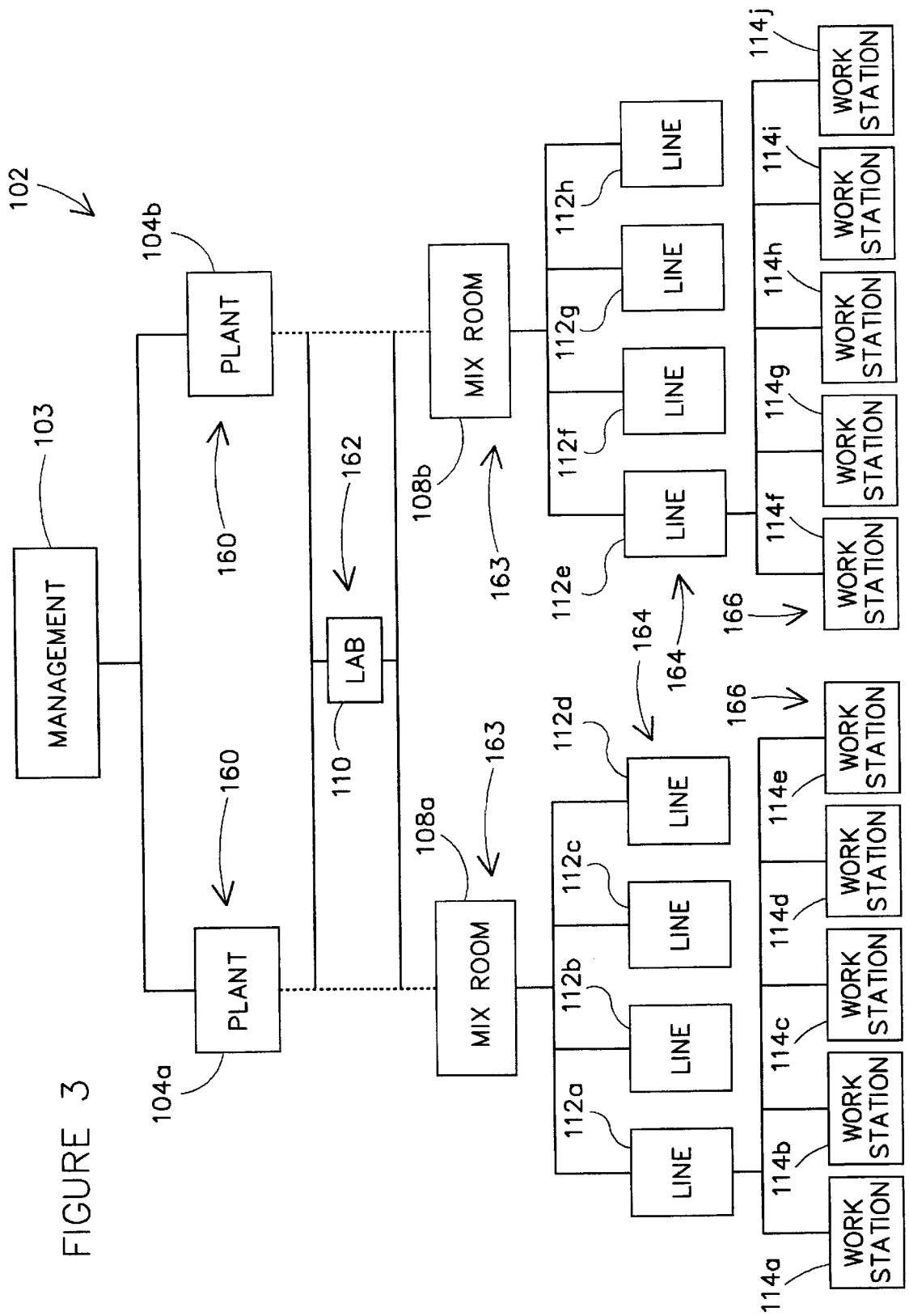
FIG. 3 is a block diagram of an enterprise for monitoring VOC emissions according to an exemplary embodiment.

Method 500 allows essentially real time accurate measurement, tracking and/or monitoring of VOC emissions for purposes of regulatory compliance. According to method 500, known information, operating parameters or data values related to the coating are collected and input in a computing device (step 502). Unknown operating parameters such as amount of coating applied by measurement of the time or flow rate (e.g., by flow monitors associated with the spray gun), temperature and humidity are also collected and input in the database (step 504). (According to an alternative embodiment, certain operating parameters or data values may be pre-programmed.) The collected operating parameters are stored in an assigned data field of a database (step 506). Calculations are performed (step 508) on the data values by a software program to determine an operating parameter related to VOC emissions (e.g., compliance with regulatory limits). Such calculations are directed to various levels of a business enterprise 102 (e.g., VOC emission for a plant, line, workstation, etc. as shown in FIG. 3). An operating parameter relating to VOC emission (e.g., total volume of VOC discharge at periodic intervals) is reported (step 510) to an end user (e.g., VOC emission for all plants in the enterprise).

Referring to FIG. 3, the amount of VOCs emitted from plant 104a is monitored across the various levels of enterprise 102. Such monitoring is useful in a jurisdiction where a regulator (e.g., enterprise, state, local and/or federal government, environmental protection agency (EPA) etc.) requires reporting of the volume of emission of VOCs. Such monitoring empowers enterprise 102 to make management decisions (e.g., amount of VOCs emitted, compliance with issued VOC emissions permits, amount of coating sprayed, etc.). A corporate headquarters or executive management 103 monitors data values related to the coating in "real time" as the workpiece is being coated in the workstations. Management 103 collects the data values "at the desktop," and does not necessarily need to be physically located on the shop floor of the workstation to ascertain how much coating has been applied and how many VOCs have been emitted by enterprise 102.

As shown in FIG. 3, an end user or manager stationed in management 103 monitors the VOC emissions produced at various levels of enterprise 102. Enterprise 102 includes a level 160 directed to facilities of the enterprise (shown as plant 104a and a plant 104b). Plant 104a may be assigned to the coating of one particular product line (e.g., seating products), and plant 104b may serve as a primary location for coating of another product line (e.g., casegoods). Plants 104a and 104b each include a level 162 having a quality assurance, test or finishing lab 110 at which analysis of the coating occurs. Lab 110 supplies data to the lines of plants 104a and 104b. The coatings are stored and mixed in mix room 108a and a mix room 108b. Mix rooms 108a and 108b supply materials and data to a line for coating the workpiece (shown as lines 112a through 12d associated with plant 104a and lines 112e through 112h associated with plant 104b) at level 163. Each line may be directed to coating a product in a product line (e.g., a particular chair in a line of seating products). Workstations 114a through 114d are associated with line 112a, and workstations 114f through 114j are associated with line 112e.

Pre-programmed or known data values related to mixing of the coating (e.g., type of coating in line, supplier, etc.) and known data values related to analysis of the coating (e.g., color, batch, amount of VOCs, percentage solids in pigment, coating viscosity, etc.) are input into a database (step 502 in FIG. 2) at level 162 for storage and analysis of the coating. Pre-programmed or known data values related to application of the coating (e.g., color, batch, etc.) are input into a database (step 502 in FIG. 2) at level 164 (e.g., at the shop floor). Measured unknown data values related to the coating (e.g., amount of coating sprayed) are input into the database (step 504 in FIG. 2) at level 166.

A corporate network of computing devices presents information in the form of data values for management to manipulate (e.g., input, program, access, monitor, modify, edit, delete, query, analyze, share, retrieve, acquire, etc.) at each level of enterprise 102 (e.g. plant mix room, lab, line and workstation, etc.). For example, management 103 may monitor the amount of VOCs emitted at the level 160, level 162, level 164, and level 166 in "real time" or simultaneously as the VOCs are emitted. According to an alternative embodiment, the management may monitor the amount of inventory (e.g., coating) sprayed at the workstation of the enterprise level, and the amount of inventory projected to be needed in the mix rooms for a period.

Figure 4:
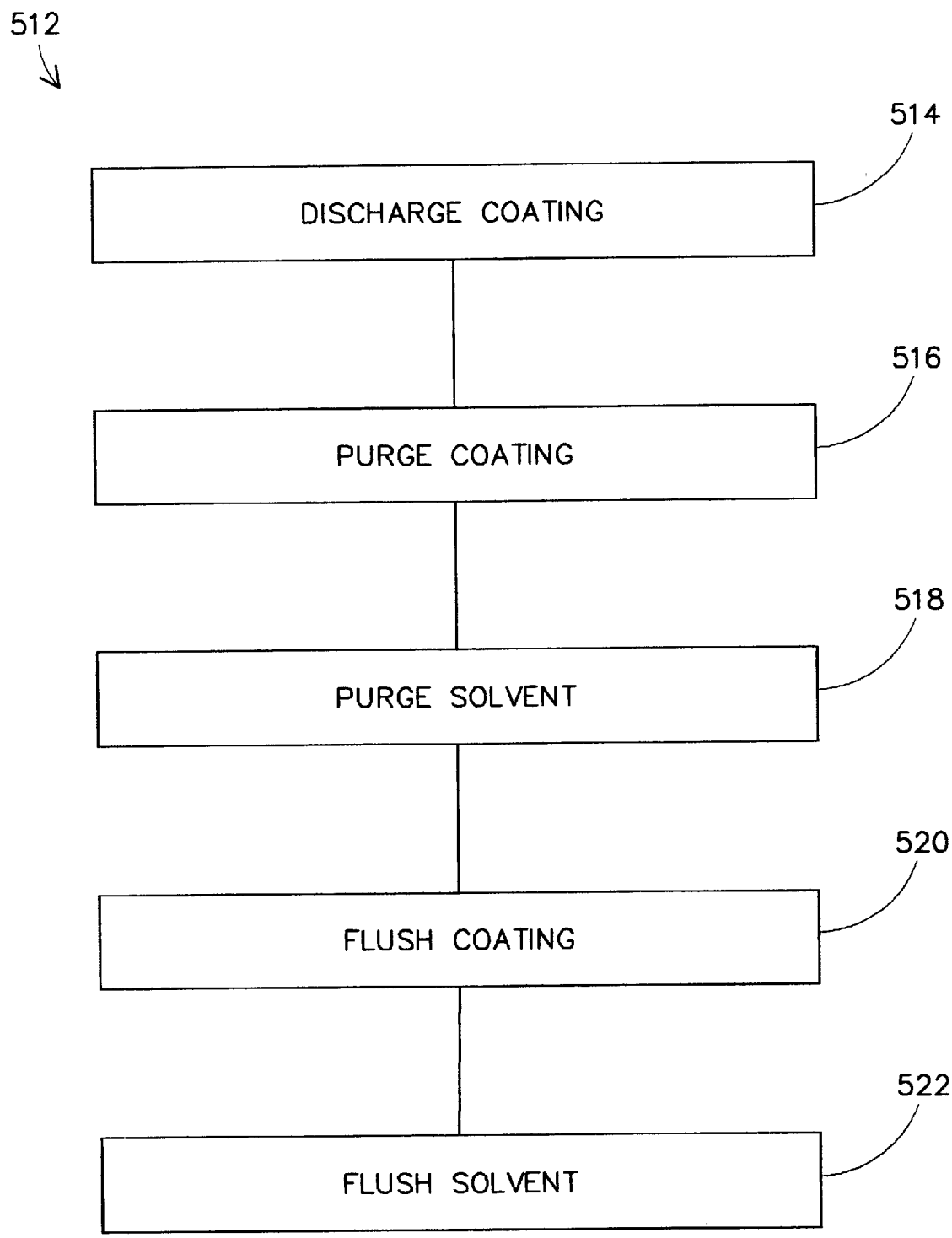
FIG. 4 is a block diagram of potential emission events according to an exemplary embodiment.
Figure 5:
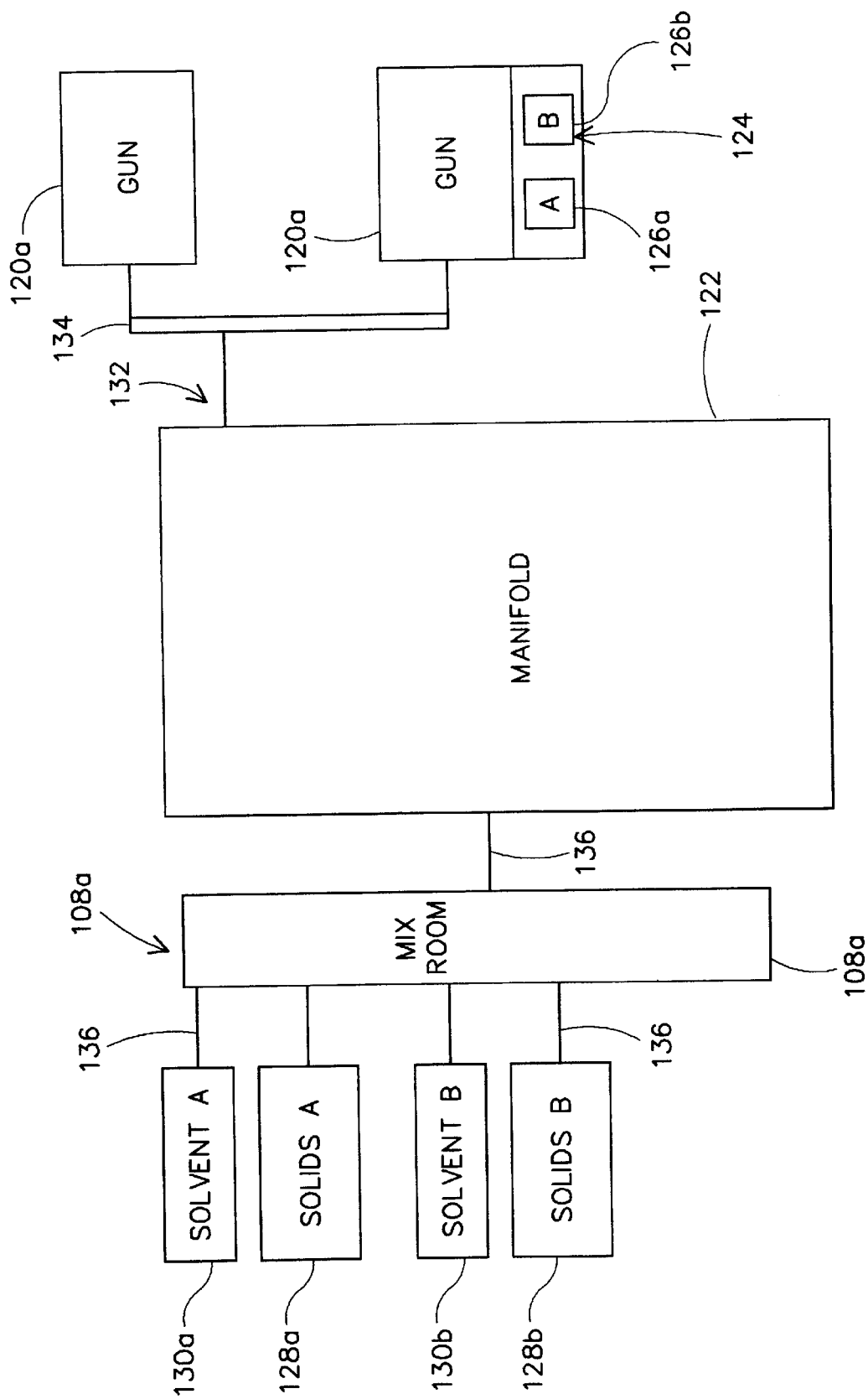
FIG. 5 is a block diagram of a coating line for providing a coating to a gun according to an exemplary embodiment.

Potential VOC emission events 512 are shown in FIG. 4. Potential emission events 512 occur as the coating is routed through line 112a and out of gun 120a. As shown in FIG. 5, a first coating type (e.g., color and batch) is selected from an input device 124 in a control booth or associated with gun 120a. (Multiple guns may be attached to a manifold or bar 134 as shown in FIG. 5. Bar may be used on an automated coating line). Input device 124 includes buttons 126a and 126b each corresponding, respectively, to raw coating source 128a and 128b and solvent source 130a and 130b. On selection of button 126a, the coating having raw coating source 128a and solvent source 130a are mixed in mixroom 108a, and the coating is routed to a manifold 122 through pipe 136. The material from raw coating source 128a and solvent source 130a is then routed to gun 120a through pipe 132. A trigger of gun 120a is depressed and the selected coating is then discharged from gun 120a onto the workpiece (step 514 in FIG. 4). The time the trigger is depressed (e.g., "trigger on"), and accordingly the time the coating is discharged (step 514 in FIG. 4), is recorded by a sensor 170a (see FIG. 6). The trigger of gun 120a may then be depressed again (e.g., "trigger off") to stop flow of the coating. VOCs may be emitted between the time the trigger is "on" and the time the trigger is "off" (step 514 in FIG. 4).

A new coating having a new color may be selected by pressing button 126b of gun 120a. The old coating is "purged" or "blipped" out of gun 120a into a storage receptacle (e.g., container, drum, bucket, etc.) for a relatively short period to remove any of the remaining old coating (e.g., from raw coating source 128a and solvent source 130a) in gun 120a (step 516 in FIG. 4). Next, the new solvent (e.g., from solvent source 130b) is "purged" or "blipped" out of gun 120a into a waste container for a relatively short period to ensure that the old coating has been removed (step 516 in FIG. 4). VOC emissions occur during the short periods of purge of the coating (step 516 in FIG. 4) and purge of the solvent (step 518). The new coating is routed from raw coating source 128b and solvent source 130b through pipe 136 to manifold 122, and then through pipe 132 to gun 120a. The previously selected coating (e.g., raw coating source 128a and solvent source 130a) is "flushed" or "dumped" back from gun 120a through pipe 132 to manifold 122 (step 520 and step 522 in FIG. 4). The flush of raw coating source 128a (step 520) and solvent source 130a (step 522) are not VOC emission events, since the raw coating and the solvent are contained by the channel and the manifold (i.e., the raw coating and the solvent do not contact the atmosphere or volatilize) in a closed system. The new coating is routed from raw coating source 128b and solvent source 130b through pipe 136 to manifold 122, and then through pipe 132 to gun 120a. The new coating is then applied to the workpieces (step 522).

Figure 6:
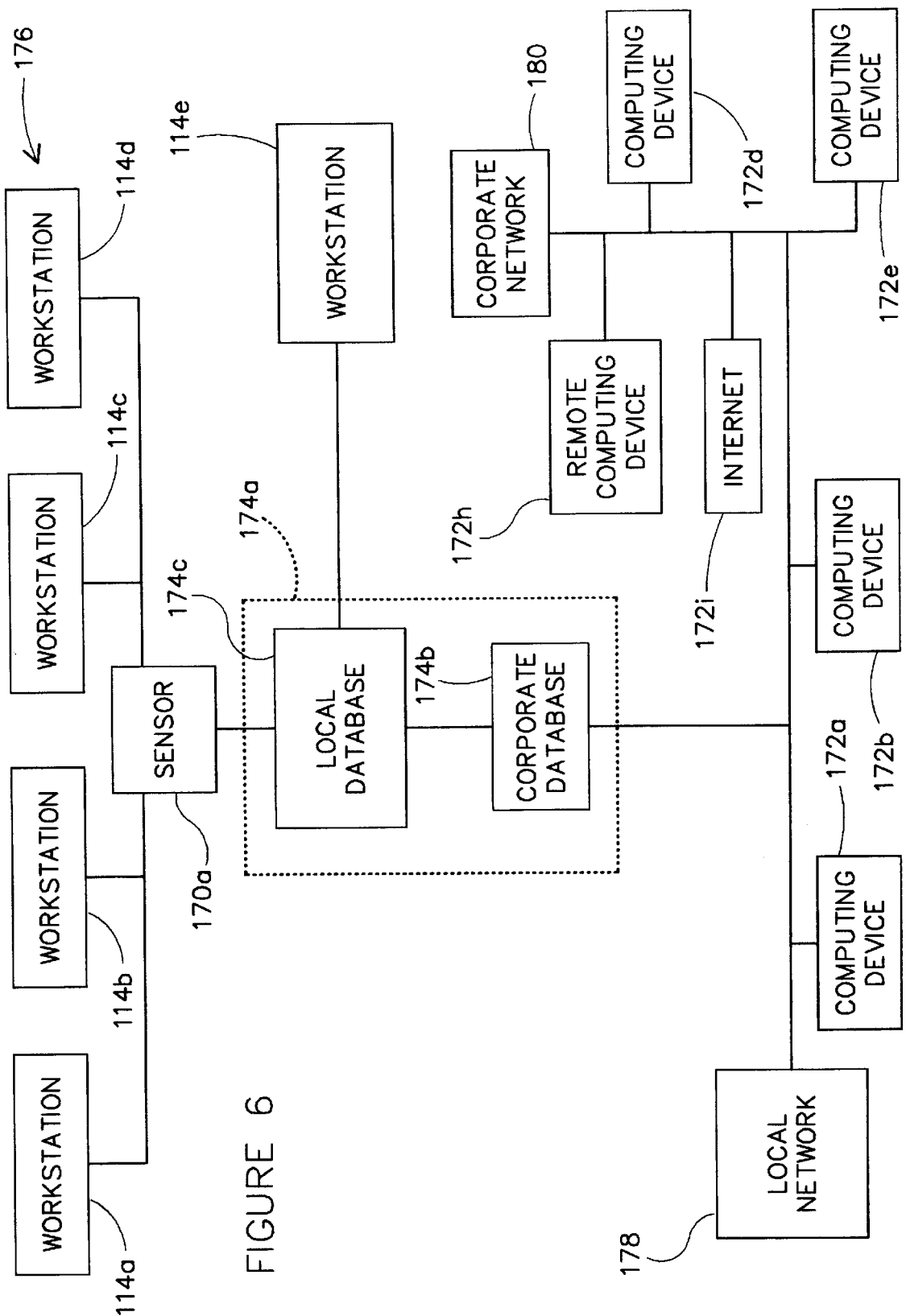
FIG. 6 is a block diagram of a monitoring system for monitoring VOC emissions according to an exemplary embodiment.

Monitoring system 100a for monitoring VOC emissions can be implemented over a network 176 as shown in FIG. 6. Workstations 114a through 114d of line 112a are shown electrically connected to sensor 170a for indicating, monitoring or counting an input signal (e.g., instantaneous, continuous, etc.) representative of an operating parameter or data value characteristic of the coating. According to alternative embodiments, the sensor may be a detector, meter, clock, memory, or connected to a programmable logic controller (PLC), etc. Sensor 170a collects data values such as duration of application or flow rate of the coating (e.g. by flow monitors associated with the gun) and a computing device (e.g. PLC) stores such data values in a register or memory. Sensor 170a provides an output signal representative of an operating parameter or data value characteristics of the coating (e.g., amount of time, amount of flow, humidity value, temperature value, etc.). The data values are stored in a data structure shown as a main or central database 174a. Central database 174a includes a corporate database 174b and a local database 174c.

Network 176 includes a local network 178 of computing devices connected to a corporate network 180 of computing devices. Certain data values are input directly to local database 174c from local network 178, and other data values are input directly to corporate database 174b from corporate network 180. For example, data values such as paint batch properties (e.g., content, makeup), painting equipment and control device properties, type of paint applied in workstation 114a are input directly into local database 174c by a computing device 172a on local network 178; data values such as VOC content in coatings are input directly into corporate database 174b by a computing device 172e on corporate network 180. Corporate network 180 is accessed by a remote computing device 172h (e.g., via dial up access) for manipulation of the data values. A computing device on Internet 172i is shown for access to network 176 and manipulation of the data values (e.g., remote or web-based access). According to a preferred embodiment as shown in FIG. 7A, local database is stored on computing device 172a (e.g., on a hard drive), and computing devices 172c and 172b access local database 174c over a network to manipulate the data values on local database 174c.

Data values are transferred between corporate database 174b and local database 174c on demand or at timed intervals (e.g., synchronized nightly or at a time when coatings are not being applied in the workstations, nightly "data dump" or downloading of data collected during a period and stored on the database, every 24 hours, etc.). The transfer of data between databases 174b and 174c permits a worker (e.g., a shop floor operator or supervisor 182) to have "instant access" to certain information (e.g., new colors and batch information as it is input into the database) on demand or at any time. The data values on corporate database 174b are manipulated by computing device 172e on corporate network 180 (e.g., an administrative or maintenance computer). Calculations (e.g., paint usage data, VOCs emitted, etc.) may be performed on the data values in a computer-based algorithm (i.e., software). The software may be on conventional computing devices. According to alternative embodiments, the computing devices may include a client server information service, a network, a remote computer, the Internet, etc.

Monitoring system 100a for monitoring VOC emissions is shown in FIG. 7A. Line 112a is shown having a workstation 114f that includes an automatically operated gun 120b controlled by a control system. Workstation 114g, which does not receive coating from the same supply as workstations 114a through 114g on line 112a, is shown "off-line" from on line 112a. Workstations 114a through 114d are shown each having a gun 120a (e.g., manually operated) connected to manifold 122 by pipe 132. Vent 142 in, each workstation is provided to route VOCs to the atmosphere. Sensor 170a is connected to gun 120a of each of workstations 114a through 114e, and a sensor 170b is associated with workstation 114f (sensor 170a is associated with workstation 114e). Sensors 170a and 170b monitor, poll, track or record the length of time each gun sprays a coating (or the amount of coating dispensed by each gun by measuring the flow of atomizing air supply), gun number, pipeline number, etc. Sensors 170a and 170b (or a computing device such as a PLC connected to the sensors) are reset or "zeroed" on a non-production day (e.g., Sunday) manually or by command from a networked computing device.

Data values from sensors 170a and 170b are input into a software program or computing device 172a intended for use on the shop floor or in association with workstations 114a through 114e. Pre-programmed or known data values (e.g., the color and batch of coating in each pipeline, the change of coating in the pipeline, etc.) are input into computing device 172b intended for use in mix room 108a and loaded into local database 174. Other pre-programmed or known data values obtained in mix room 108a include the amount in gallons, the model, and the batch number for each batch of paint, the amount in gallons, the solvent identification for solvent added to the solids of the coating, applicator type, and the ratio of raw coating source to solvent source in the coating. These data values are loaded into corporate database 174b. In a similar manner, data values such as color, batch, pigment/solvent ratio for the coatings applied in workstation 114g are input into a computing device 172c associated with workstation 114g and loaded into local database 174c.

Other data values are down loaded to corporate database 174b. Data values related to the coating, such as information provided by the coating supplier, VOC content, transfer efficiency (determined for example by the United States EPA New Source Performance Standards (NSPS) subpart EE for metal furniture surface), pounds of VOC per gallon of raw paint (e.g., from paint suppliers for every batch of paint received by the company), raw VOC content, density, solids content, reducer pounds of VOC, etc., are input into a computing device 172d intended for use by a finish technician in lab 110 and loaded into corporate database 174b. All data values in corporate database 174b may be manipulated by computing device 172e intended for use by a maintenance personnel or system or database administrator 190. Any data values containing errors are manipulated (e.g., corrected) by computing device 172e. Computing device 172e is also used to add or configure new equipment (e.g., pipeline, workstation, gun, etc.) in monitoring system 100a. Certain data values (e.g., relating to amount of coating sprayed, flow rates, environmental data, paint consumption data, etc.) are manipulated (e.g., accessed, queried, etc.) from corporate database 174b by a computing device 172f for an end user or manager 186. The data values may be presented in a report (see FIGS. 14A through 14G).

Monitoring system 100a provides for integrity of the data values by providing access and security controls. For example, supervisor 182 may only access certain data values in local database 174c by computing device 172a, and is limited from accessing other data in the corporate database 174b and local database 174c (based on permissions set by a database administrator). Such limitation of access provides enhanced security for the data values in database 174a, and reduces the likelihood of user error. For example, supervisor 182 may only select the color and batch of the coating to be sprayed. A mix room operator 194 may only input the color and batch information in local database 174c. Corrections can be made by the appropriate individual (e.g., administrator 190) with the appropriate level of access to correct the data values. For example, mix room operator 194 or administrator 190 may correct information related to a color or batch, but the supervisor 182 can only select the information provided by the mix room. Thus, the scope, access or permissions of users of the data values may be limited.

According to alternative embodiments, the computing device may be a PDA, PC, microcomputer, portable computer, digital device, programmable logic controller (PLC), etc. According to a preferred embodiment, the computing device is a WinNT workcell device or a WIN 95 computing device. According to an alternative embodiment, the software associated with the computing device for the input of information may be a C++ application using Pro/C and SQL Net. According to a preferred embodiment, the software used to generate the reports is Business Objects software commercially available from Business Objects, S.A. of Paris, France. According to a preferred embodiment, the corporate database is an Oracle server commercially available from Oracle Corporation of Redwood Shores, Calif., and the local database is an Oracle database commercially available from Oracle Corporation of Redwood Shores, Calif. According to an alternative embodiment, an Intranet or the Internet may connect the database to the computing devices. According to a particularly preferred embodiment, the network connection for the computing devices is provided by a serial port connection. According to a preferred embodiment, the computer software for providing communication between the computing devices (e.g., personal computers) and programmable controllers (e.g., PLC) used in the monitoring system is RSLINX software commercially available from Rockwell Software, Inc. of Cleveland, Ohio.

The PLC may be a controller or programmable PLC for implementing a control program and which provides output signals based on input signals provided by an operator or otherwise acquired. PLC may have an A/D (analog-to-digital) converter to convert analog signal from the sensor to digital. According to alternative embodiments, other suitable controllers of any type may be included in the control system. For example, controllers of a type that may include a microprocessor, microcomputer or programmable digital processor, with associated software, operating systems and/or any other associated programs to collectively implement the control program may be employed. According to alternative embodiments, the controller and its associated control program may be implemented in hardware, software or a combination thereof, or in a central program implemented in any of a variety of forms. According to a particularly preferred embodiment, input to the control program is provided by turning a trigger of the gun "on" and the control program performs operations (i.e., sending signals to a computing device) while the trigger is "on" and for a period after the trigger is turned "off."

Figure 7B:
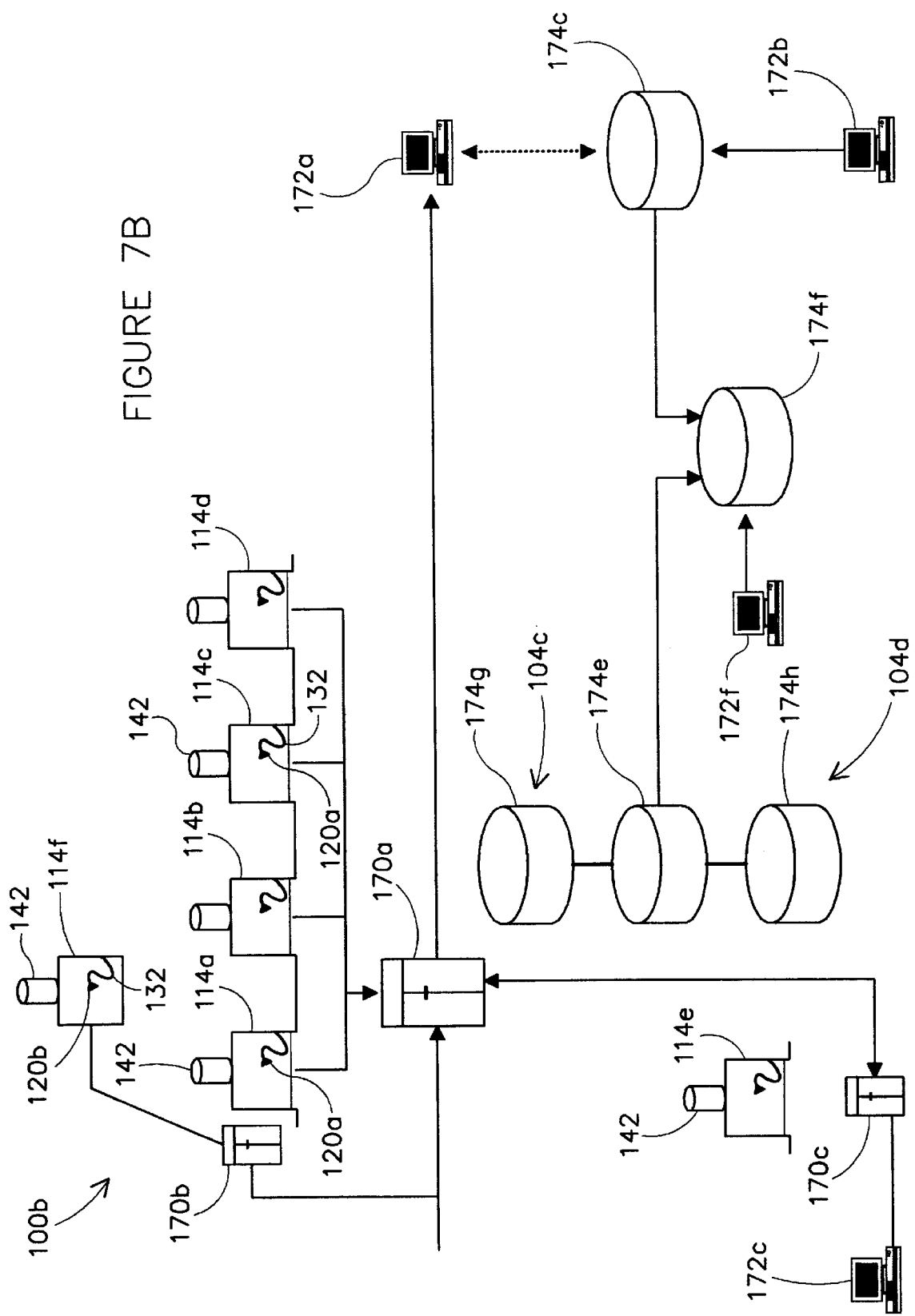
FIG. 7B is a schematic diagram of a monitoring system for monitoring VOC emissions according to an alternative embodiment.

A monitoring system 100b for monitoring VOC emissions is shown in FIG. 7B according to an alternative embodiment. Monitoring system 100b differs from monitoring system 100a in at least the following respects: computing device 172c associated with workstation 114e does not have immediate or "on demand" access to the data values in local database 174c; computing device 172c is not on local network 178; and multiple corporate databases are connected to a local database. Data values for the enterprise, such as those relating to VOC content, color, batch, etc., are stored on a local database 174e (e.g., Access software commercially available from Microsoft Corporation of Redmond, Wash.) on a computing device. Data values may be temporarily stored in a local database 174d (e.g., in Access software commercially available from Microsoft Corporation of Redmond, Wash.) from computing device 172a intended for use on the shop floor and computing device 172b intended for use in mix room 108a. The data values are transferred nightly to a permanent shared database 174f (e.g., a NSPS file share database running Access software commercially available from Microsoft Corporation of Redmond, Wash.). Other data values such as VOC content are input directly into shared database 174f or downloaded from local database 174e. An environmental technician or end user 186 with access to shared database 174f through computing device 172f may query the data values to produce environmental and paint consumption reports (i.e., in Access software commercially available from Microsoft Corporation of Redmond, Wash.). A corporate database 174g associated with a plant 104c of the enterprise, and a corporate database 174h associated with a plant 104d of the enterprise, are shown having shared access to local database 174e. Corporate databases 174g and 174h include data values from local databases associated with plants 104c and 104d, respectively.

Figure 8:
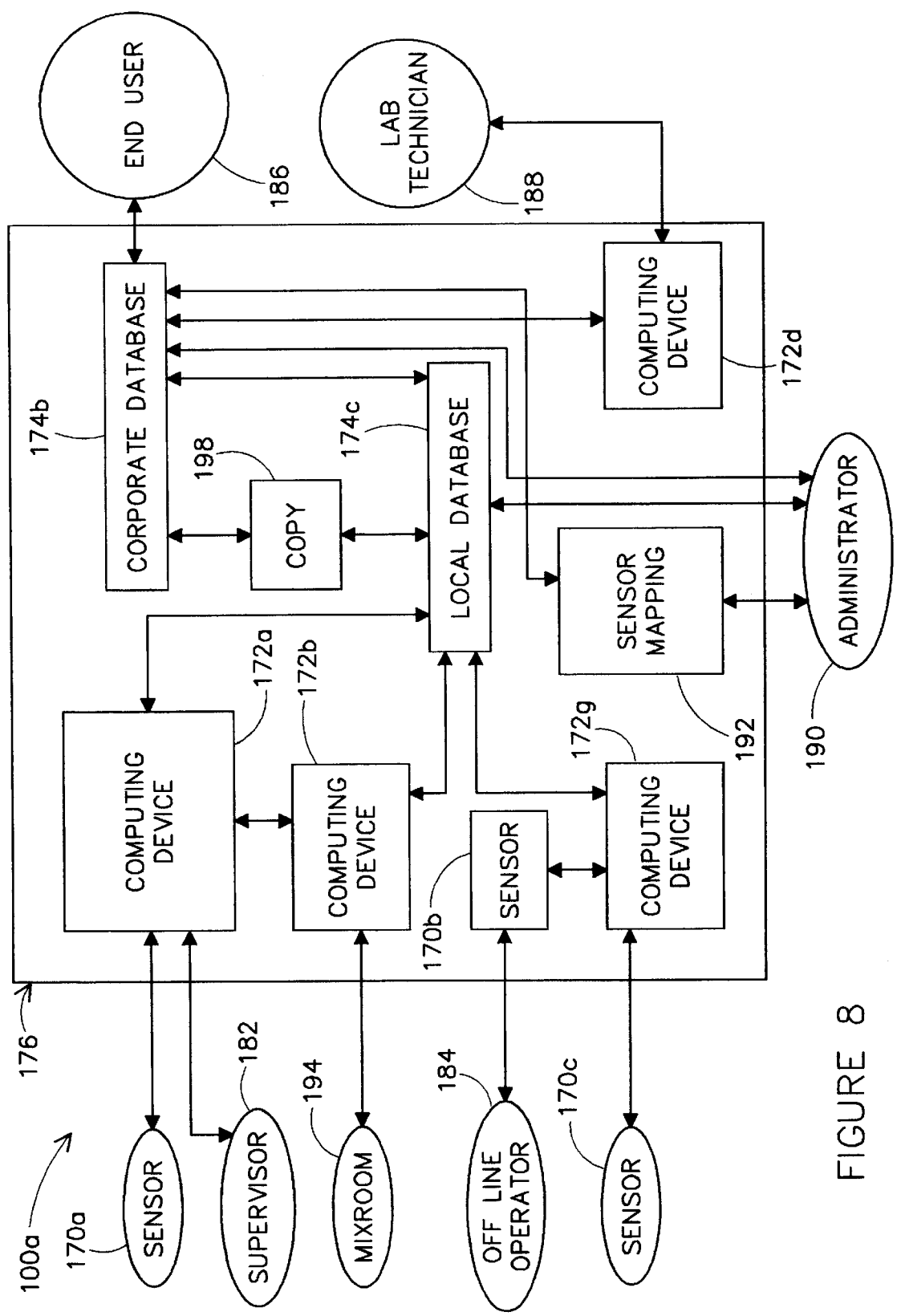
FIG. 8 is a block diagram of a data collection system according to a preferred embodiment.

A data flow diagram of the flow of data values in system 100a is shown in FIG. 8. Data values relating to time a coating is applied in workstation 114a are read by sensor 170a for measuring trigger time. These data values are input into computing device 172a intended for use on the shop floor, and downloaded to local database 174c. In a similar manner, data values relating to flow rate are read by sensor 170b (for measuring flow amount), input into computing device 172a, and downloaded to local database 174c. Supervisor 182 has manual access to sensors 170a and 170b or access through computing device 172a and 172g.

Data values relating to a pipeline change are input into computing device 172b intended for use in mix room 108a. Such data values include what color and batch of coating is in each pipeline. Data values relating to the time a coating is applied in workstation 114g are read by sensor 170a for measuring the rate of coating in workstation 114g, and the color and batch sprayed in workstation 114g. These data values are input into computing device 172c associated with sensor 170b and downloaded to local database 174c (see FIG. 7A).

Lab technician 188 can use computing device 172d to supply paint data relating to VOC content in each batch of coating. End user 186 can generate a report relating to the coating by querying the data values on corporate database 174b. Administrator 190 can map the data values (shown as sensor mapping 192) in each of sensors 170a and 170b in monitoring system 100a. Specifically, administrator 190 assigns which registers of the sensors (e.g., PLC) are used to record certain operating parameters, so data values in those registers may be quickly and easily downloaded to local database 174c. Administrator 190 may also calibrate the sensors after operational changes such as a change in color to be sprayed.

Administrator 190 has access and control over the entirety of monitoring system 100a. For example, administrator 190 may reset the registers of sensors 170a and 170b at will, and may obtain data values stored in the sensors on demand. Administrator 190 may access local database 174c and corporate database 174b to manipulate the data values. Administrator 190 may manipulate the data values in corporate database 174b, which are then copied or synchronized (copy 198) with the data values in local database 174c. These data values are then updated on computing devices 172a, 172b and 172c. According to an alternative embodiment, administrator 190 may manipulate (e.g., modify) any erroneous data at level 160, level 162, level 164, and level 166 in enterprise 102 (see FIG. 3).

Figure 9A:
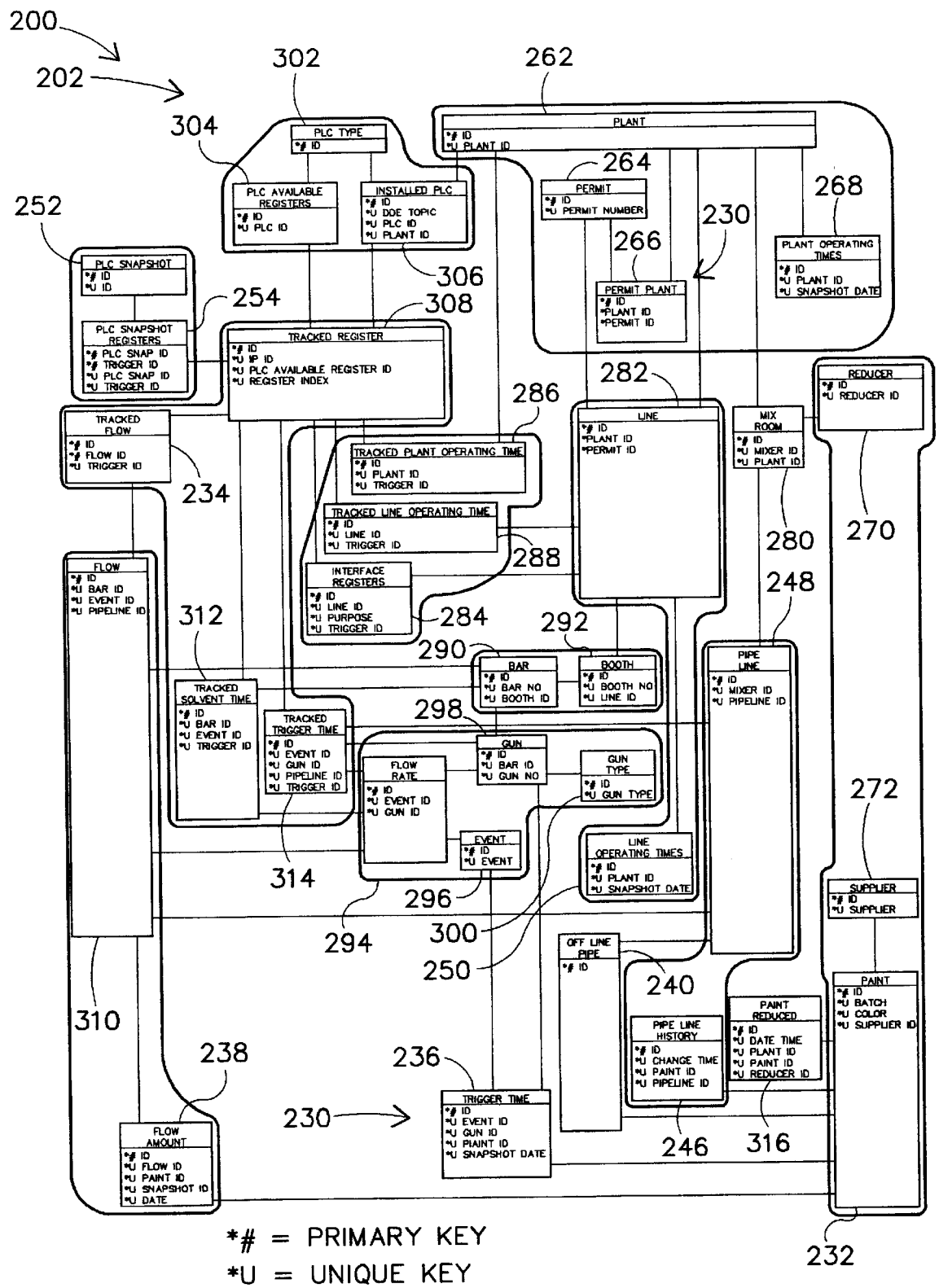
FIG. 9A is a block diagram of a global database scheme according to a preferred embodiment.

FIG. 9A shows a global database scheme 200 of the structure and arrangement of tables 230 in database 174a. Each table 230 in database 174a includes data fields (e.g., attributes, column heading, field, etc.) for recording data values (e.g., records, rows, values, etc.). Tables 230 in database 174a are related or linked to each other by a "foreign key," and are arranged in groups or modules 202. Such linking of the tables assists in arranging the data fields to assist in minimizing user error during input of data values. According to a particularly preferred embodiment, the database is an Oracle database commercially available from Oracle Corporation of Redwood Shores, Calif.

Integrity of the data values is maintained by using referential integrity constraints. Integrity constraints assist in enforcing the business rules associated with database 174a and prevent the entry of invalid information into tables 230. Integrity constraints include "not null" constraints (identified in FIGS. 9A and 9B by a "*" symbol), "primary key" constraints (identified in FIGS. 9A and 9B by a "*#" symbol), "unique key" constraints (identified in FIGS. 9A and 9B by a "*U" symbol), and "foreign key" constraints.

Not null integrity constraints for data fields (e.g., column) generally require data values (e.g., in a row of data for an identified column at all times). Not null constraints are often combined with other types of integrity constraints (e.g., primary key, unique key, foreign key, etc.) to restrict the values that can exist in specific columns of a table. Each table 230 in database 174a is shown having one primary key constraint. The purpose of the primary key is to identify a unique row of the table. A primary key allows each row in a table to be uniquely identified and ensures that no duplicate rows exist. Each of tables 230 in database 174a is shown having a unique key constraint. No row in table 230 duplicates a value in the data fields (e.g., column) of the unique key constraint. A foreign key constraint (not shown) may be used whenever a common column (or set of columns) relates two tables. The foreign key is typically defined in the "child" table to maintain the relationship between the two tables.

Providing referential integrity in tables 230 yields data values that are in "third normal form." For example, each paint identified in a table 232 showing paint information includes a primary key field (shown as an #id field 204) and a unique key (shown as a color field 206). Likewise, tracked flow information in a table 234 is shown having a primary key (shown as a tracked flow identification field 208) and a unique key (shown as a trigger identification 210).

Some data values are input directly into local database 174c, and other data values are input directly into corporate database 174b. The data values in corporate and local databases 174b and 174c are "synchronized" periodically. According to a particularly preferred embodiment as shown in FIG. 9A, the data values for the following tables are directly input into local database 174c: trigger time table 236, flow amount table 238, offline pipeline table 240, pipeline history table 246, pipeline table 248, line operating time table 250, PLC snapshot table 252, and PLC snapshot register table 254. All other data values are directly input into corporate database 174b.

A table 254 showing contact information includes a primary key (shown as an id field 212) identified by a "*#" symbol. ID field 212 is a required or not null field (identified by a "*" symbol) as shown in FIG. 9B. Table 254 is not necessarily related to any other table in database 174a. Other fields such as "fax number" is an "optional" or null field (identified by an "O" symbol). Database 174a includes "views" or temporary tables or screens for viewing data values. ID field 212 requires a numeric data value (identified by a "789" symbol). Other fields such as "last name" require an alphanumeric data value (identified by an "A" symbol). FIGS. 9C through 9E show exemplary views relating to batch content of the coating. The views shown in FIGS. 9C–9D do not necessarily require a primary key, and the views shown in FIGS. 9C and 9E do not necessarily require a unique key.

Figure 10A:
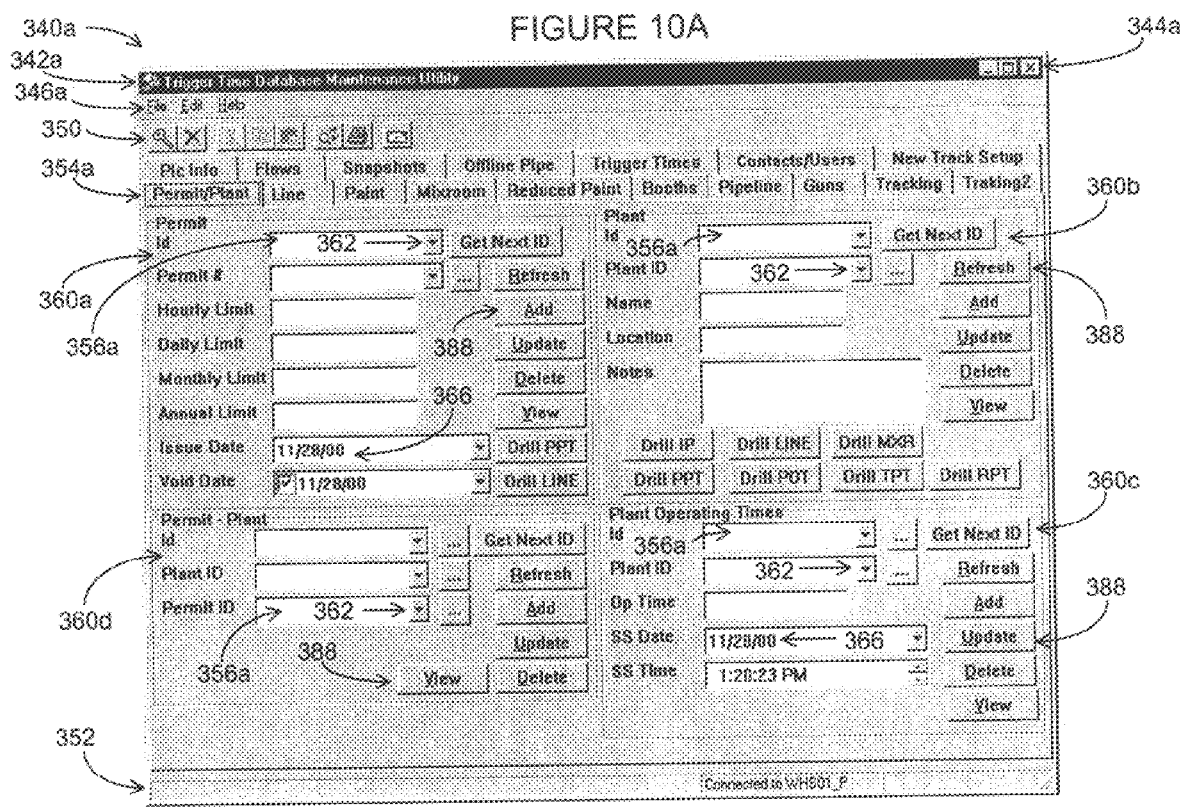
FIG. 10A is a user interface showing permit information and intended for interaction with an operator via a computing device according to an exemplary embodiment.
Figure 10C:
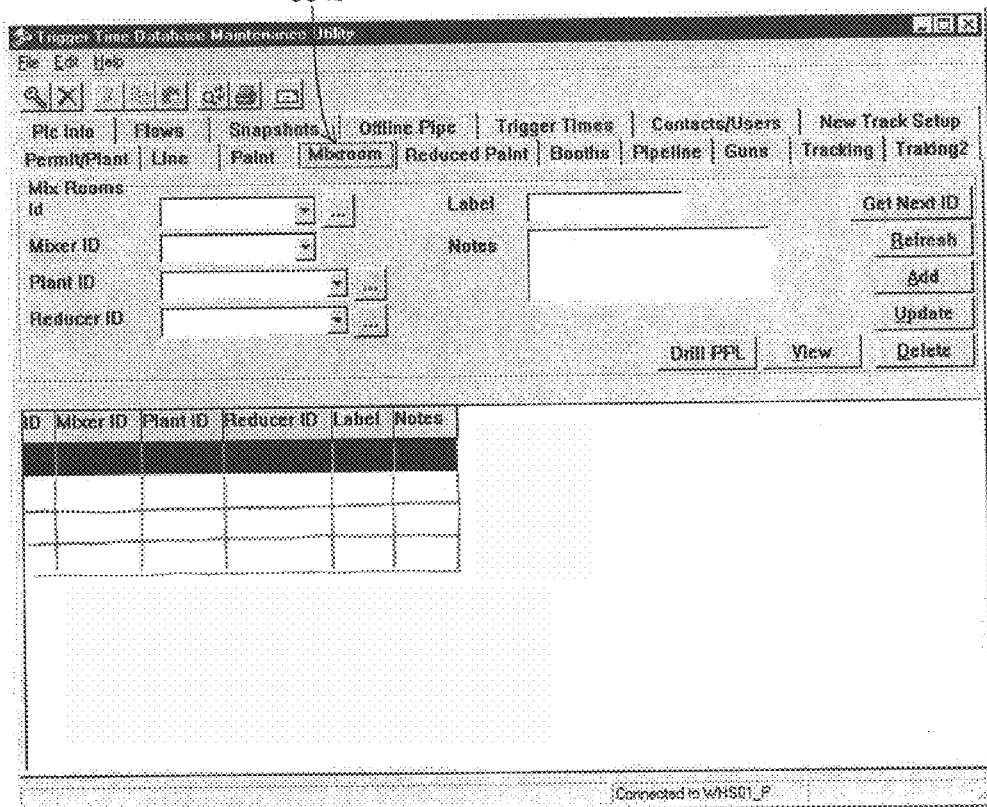
FIG. 10C is a user interface showing mix room information and intended for interaction with an operator via a computing device according to an exemplary embodiment.
Figure 10D:
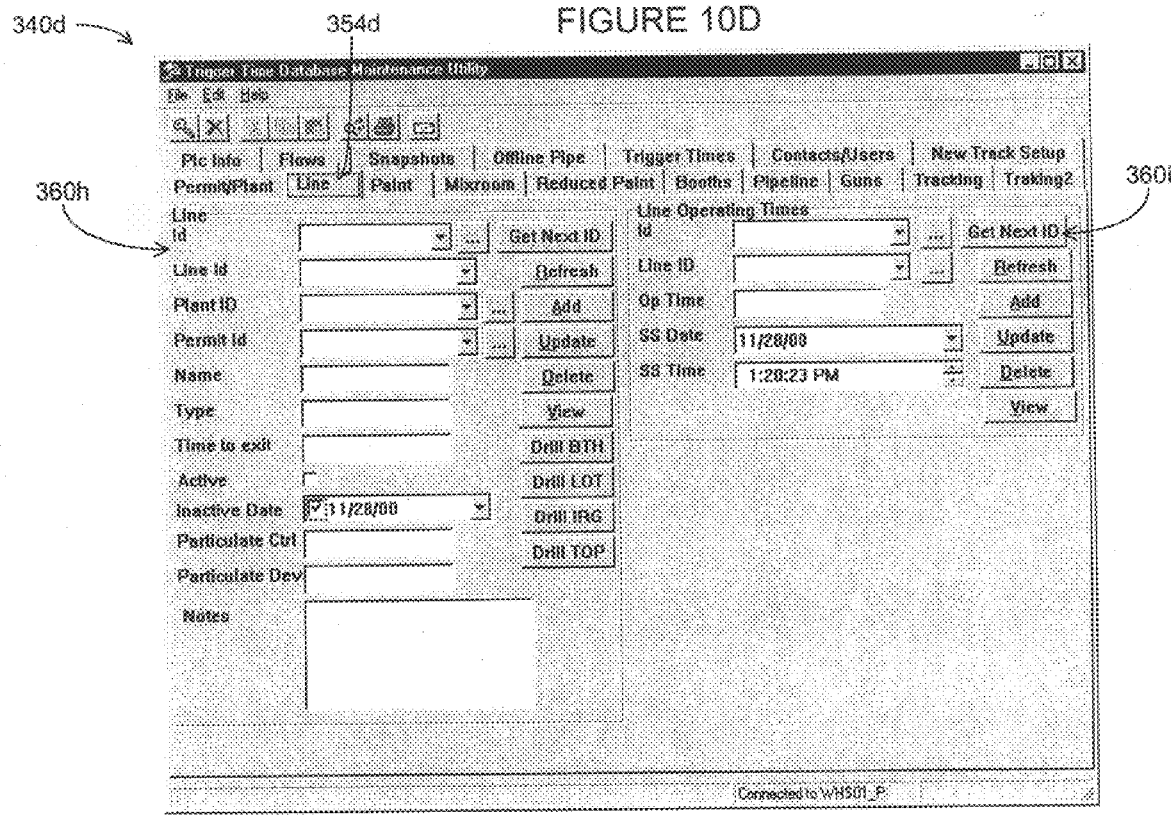
FIG. 10D is a user interface showing line information and intended for interaction with an operator via a computing device according to an exemplary embodiment.
Figure 10E:
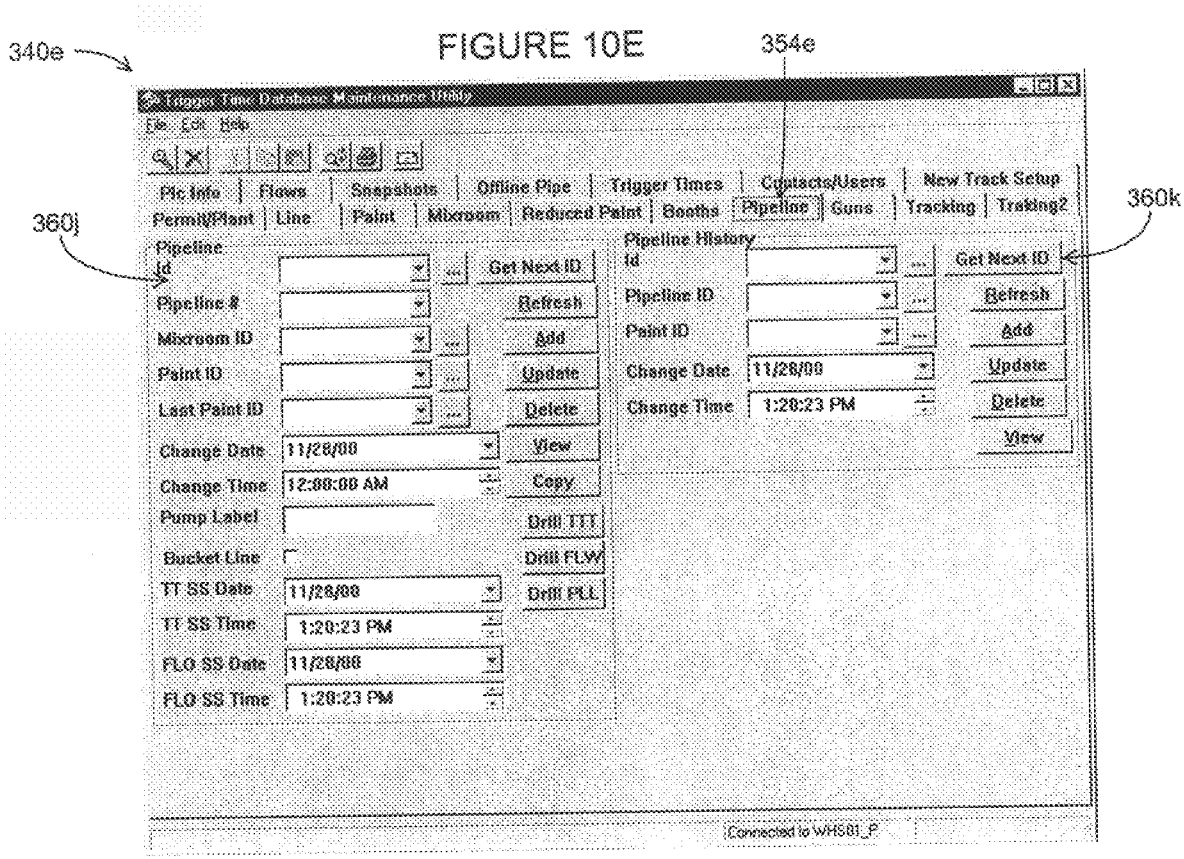
FIG. 10E is a user interface showing pipeline information and intended for interaction with an, operator via a computing device according to an exemplary embodiment.
Figure 10F:
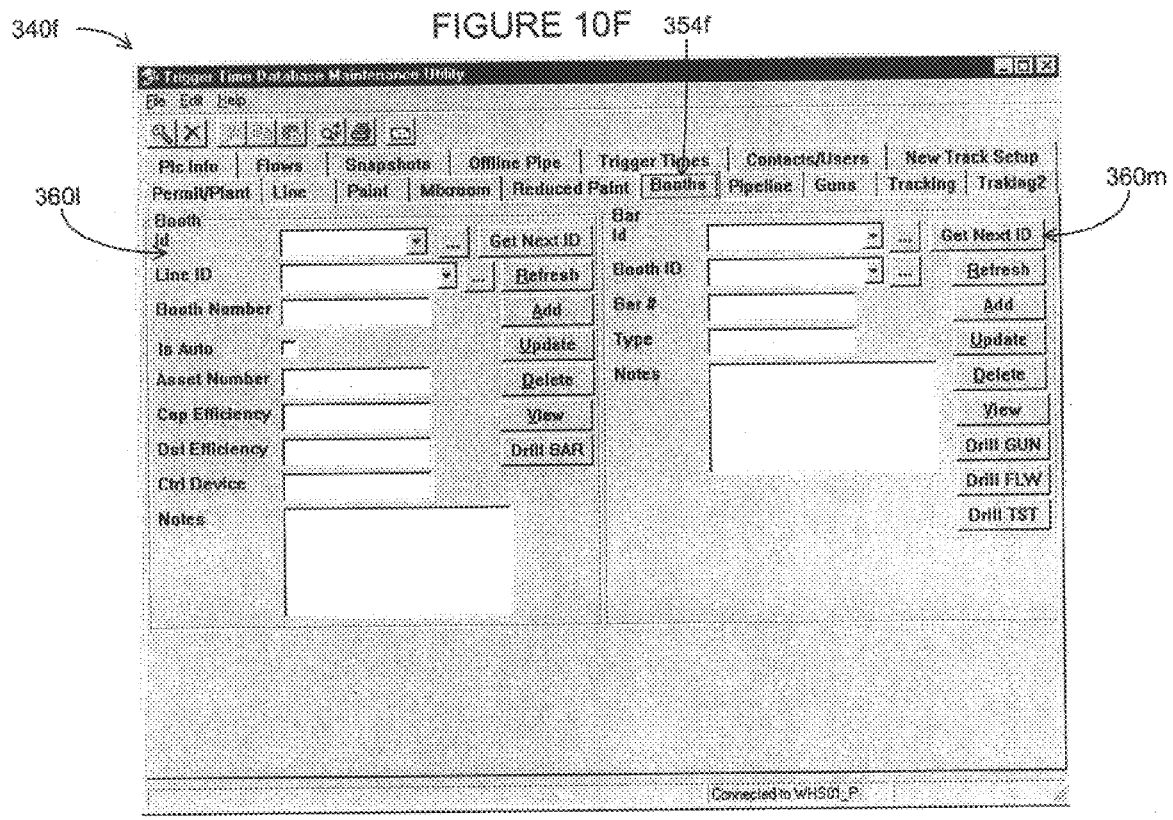
FIG. 10F is a user interface showing booth information and intended for interaction with an operator via a computing device according to an exemplary embodiment.
Figure 10G:
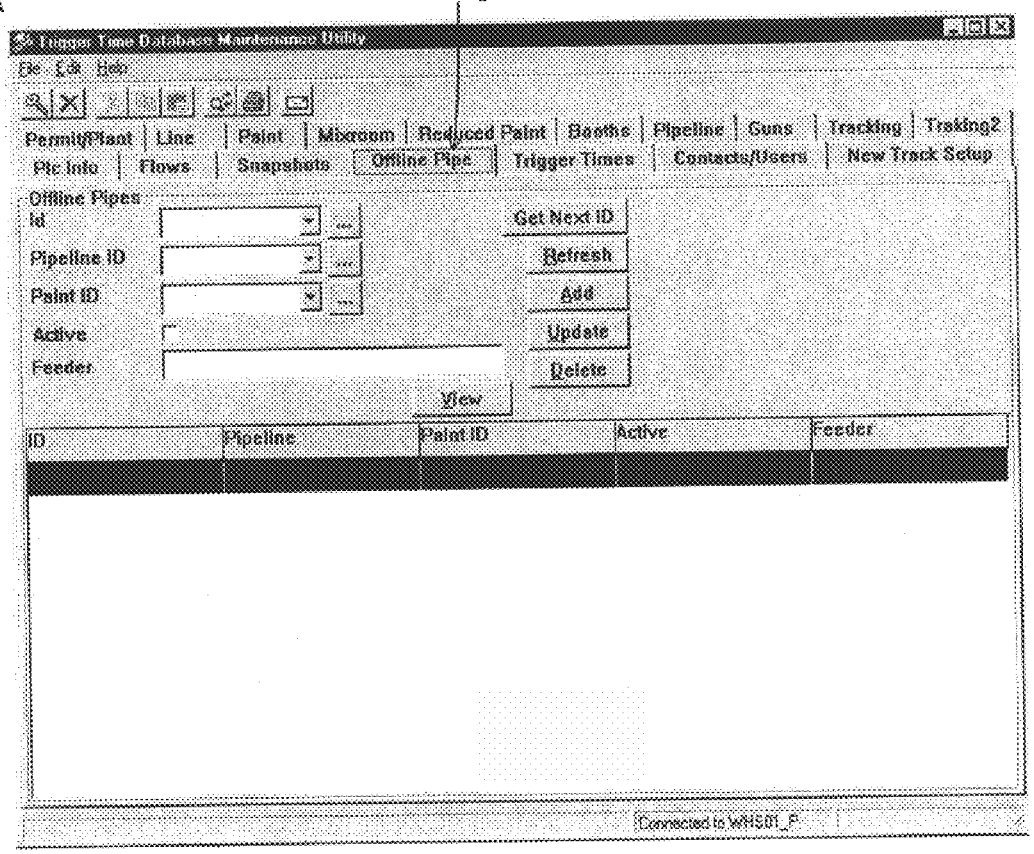
FIG. 10G is a user interface showing offline pipe information and intended for interaction with an operator via a computing device according to an exemplary embodiment.
Figure 10H:
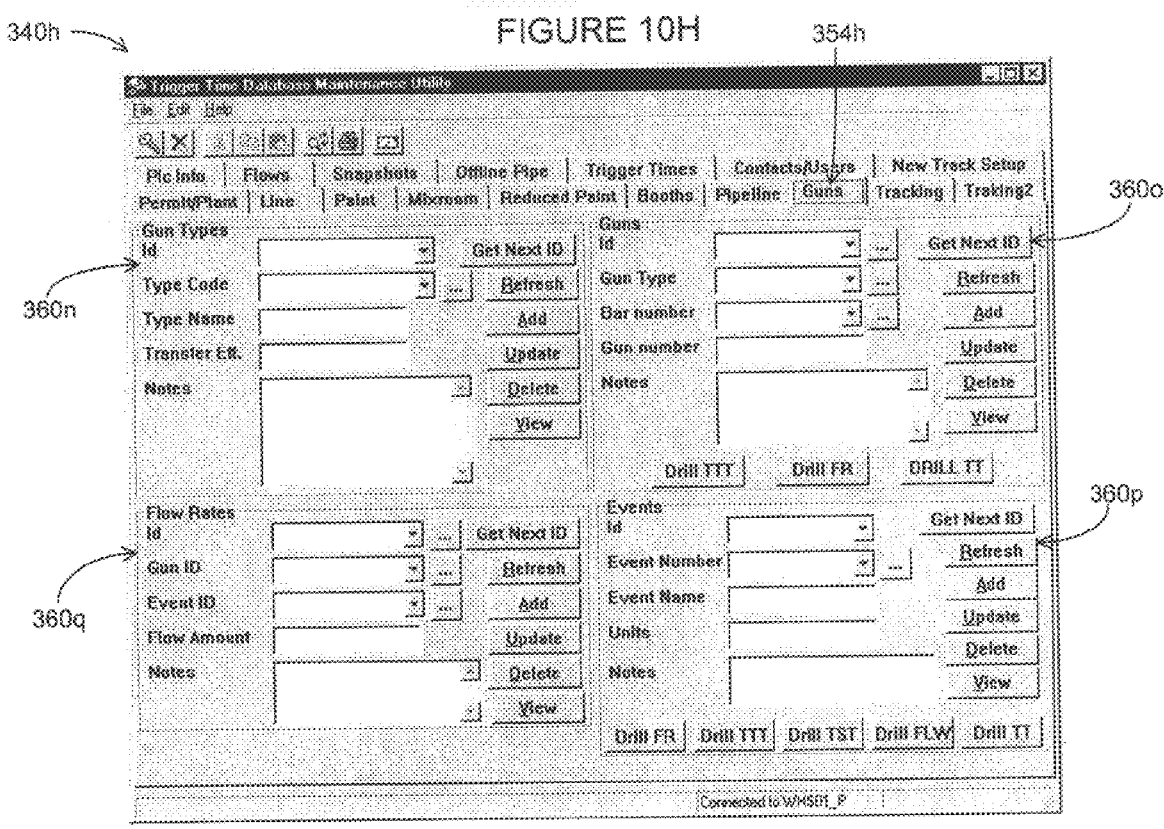
FIG. 10H is a user interface showing gun information and intended for interaction with an operator via a computing device according to an exemplary embodiment.
Figure 10I:
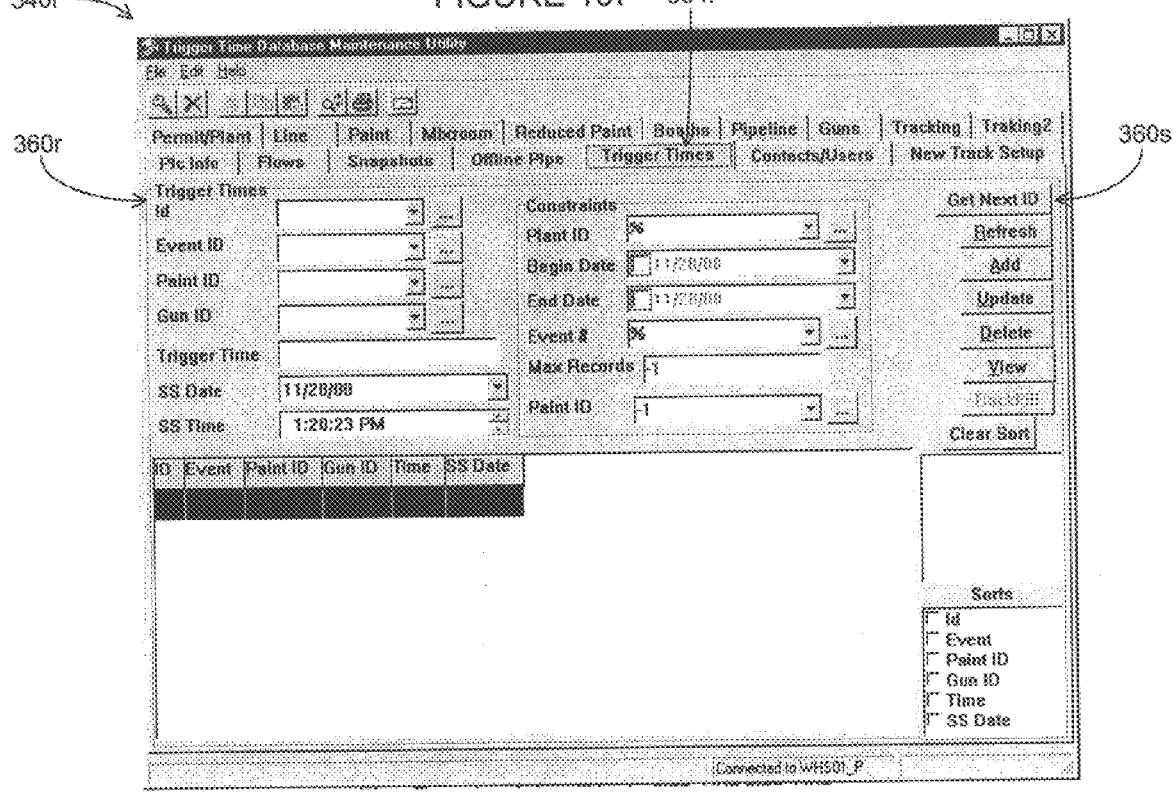
FIG. 10I is a user interface showing trigger time information and intended for interaction with an operator via a computing device according to an exemplary embodiment.
Figure 10J:
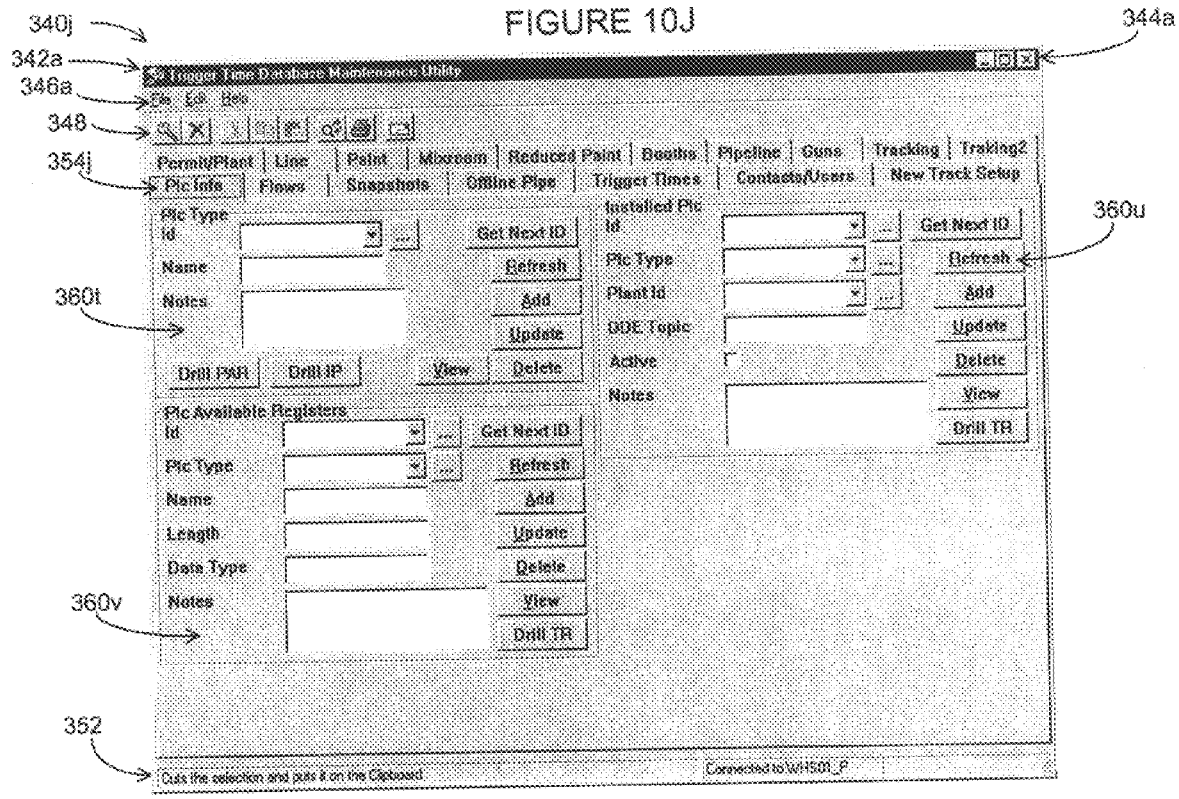
FIG. 10J is a user interface showing PLC information and intended for interaction with an operator via a computing device according to an exemplary embodiment.
Figure 10K:
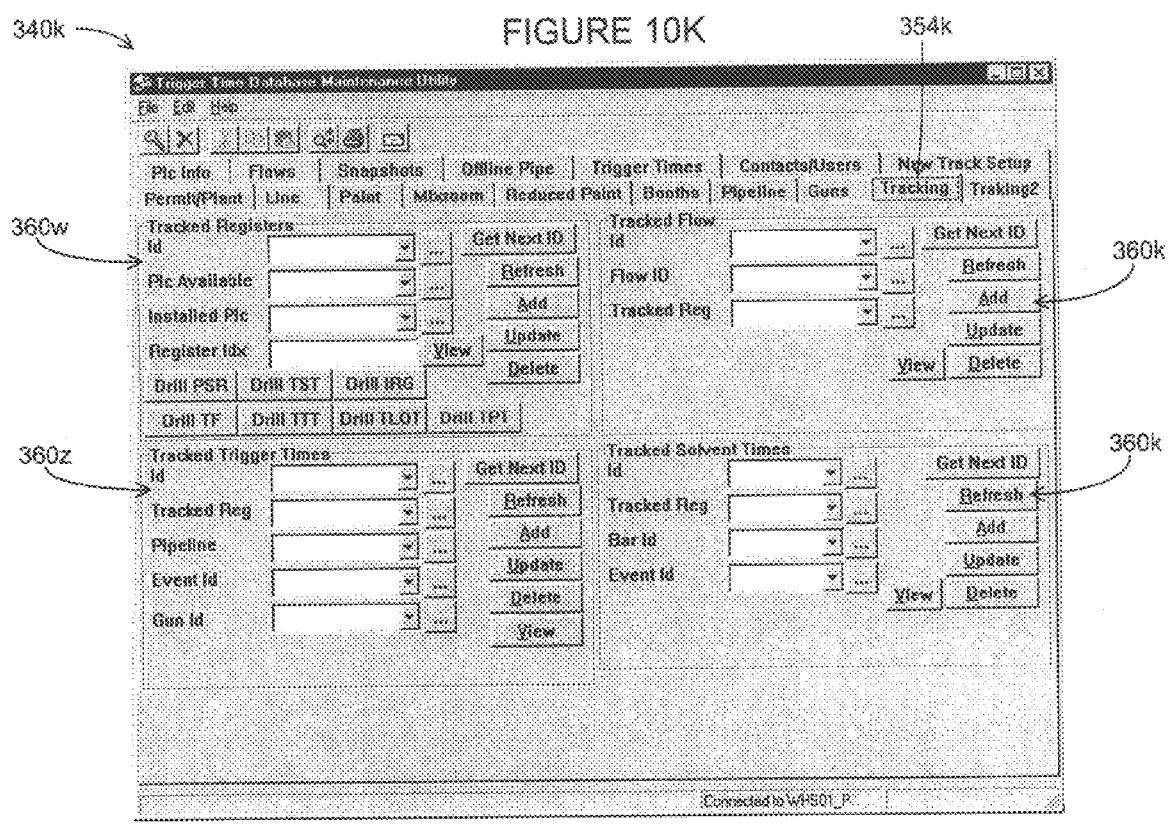
FIG. 10K is a user interface showing tracking information and intended for interaction with an operator via a computing device according to an exemplary embodiment.
Figure 10L:
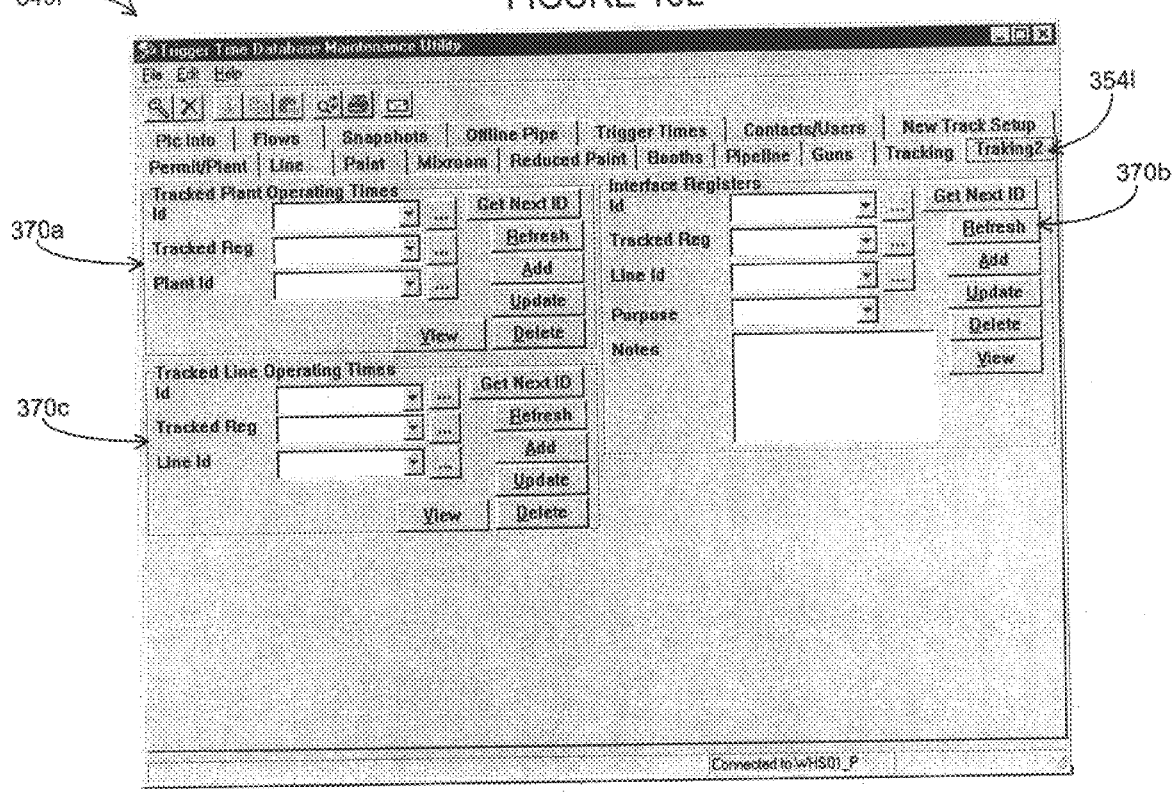
FIG. 10L is a user interface showing tracking information and intended for interaction with an operator via a computing device according to another exemplary embodiment.
Figure 10M:
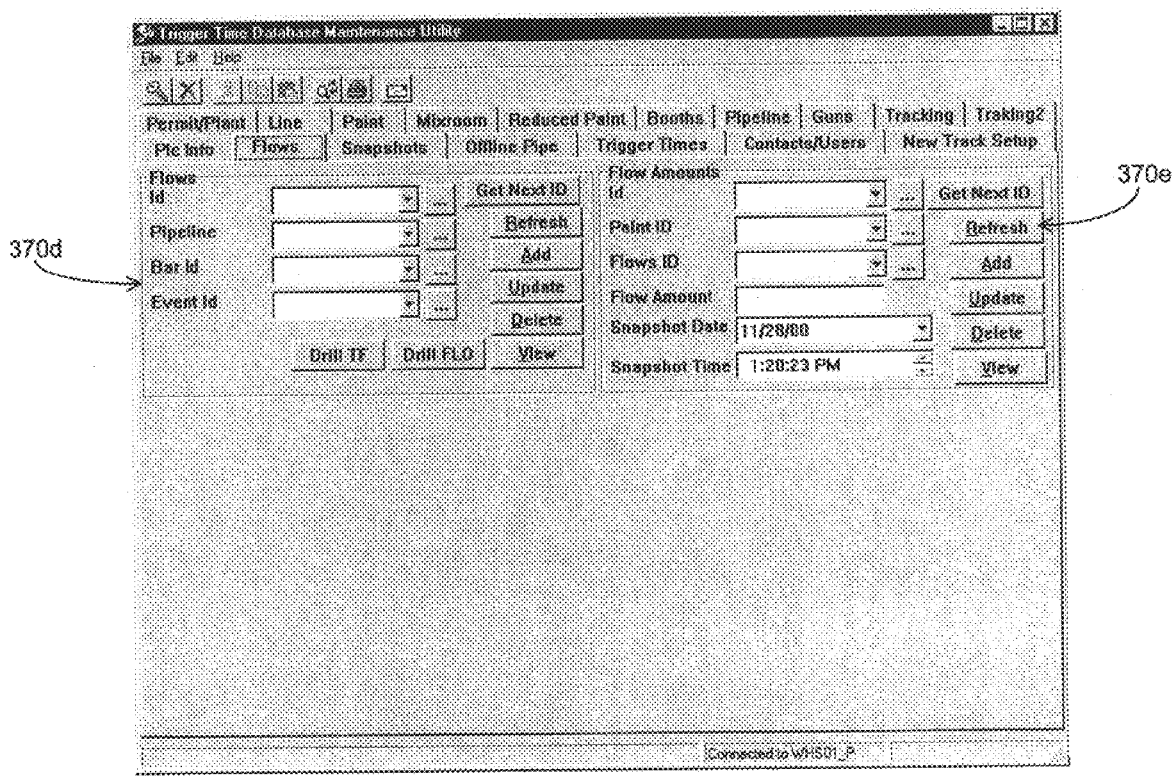
FIG. 10M is a user interface showing flow information and intended for interaction with an operator via a computing device according to an exemplary embodiment.
Figure 10N:
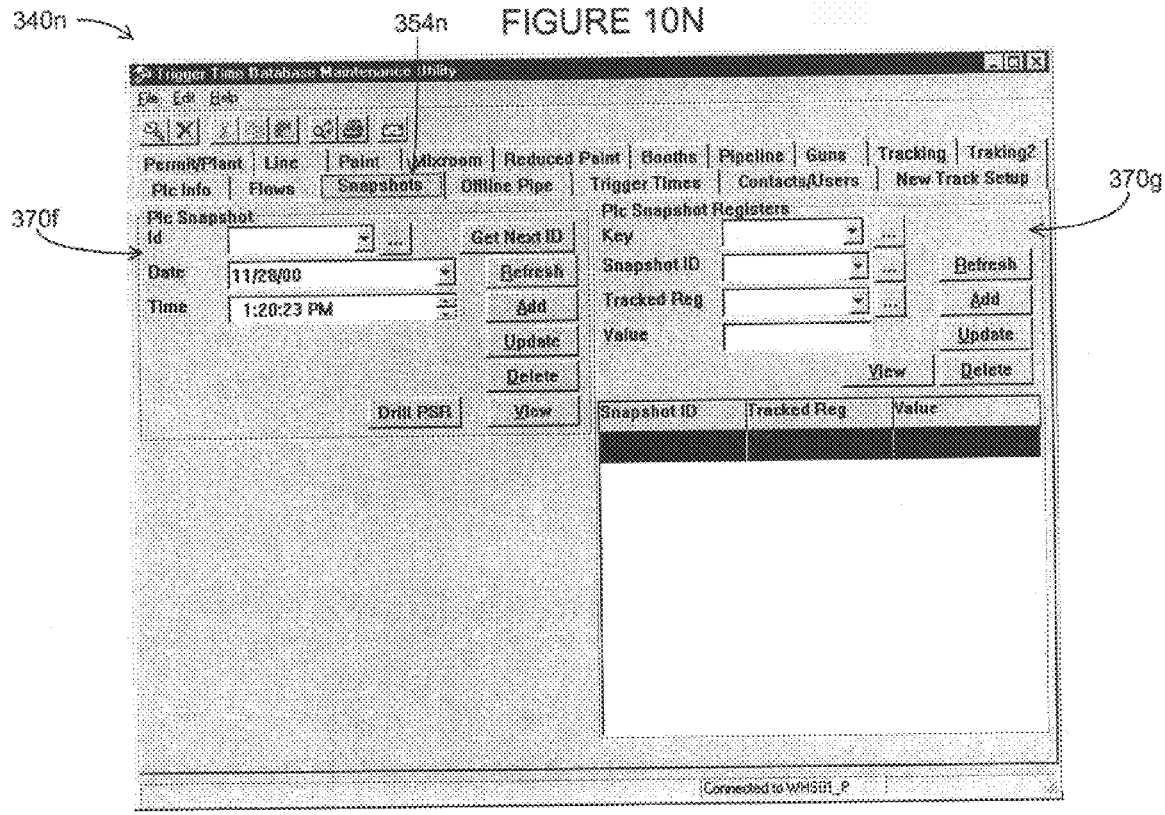
FIG. 10N is a user interface showing snapshot information and intended for interaction with an operator via a computing device according to an exemplary embodiment.
Figure 10O:
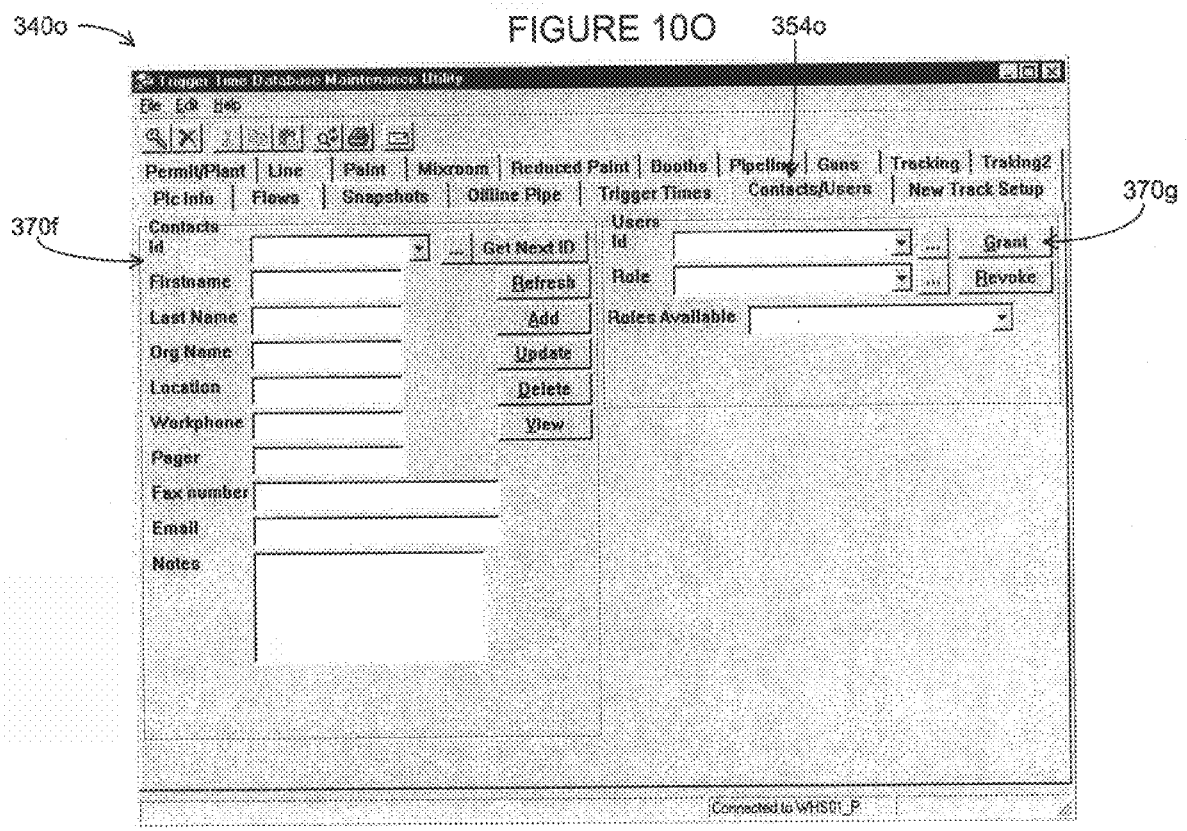
FIG. 10O is a user interface showing contact information and intended for interaction with an operator via a computing device according to another exemplary embodiment.
Figure 10P:
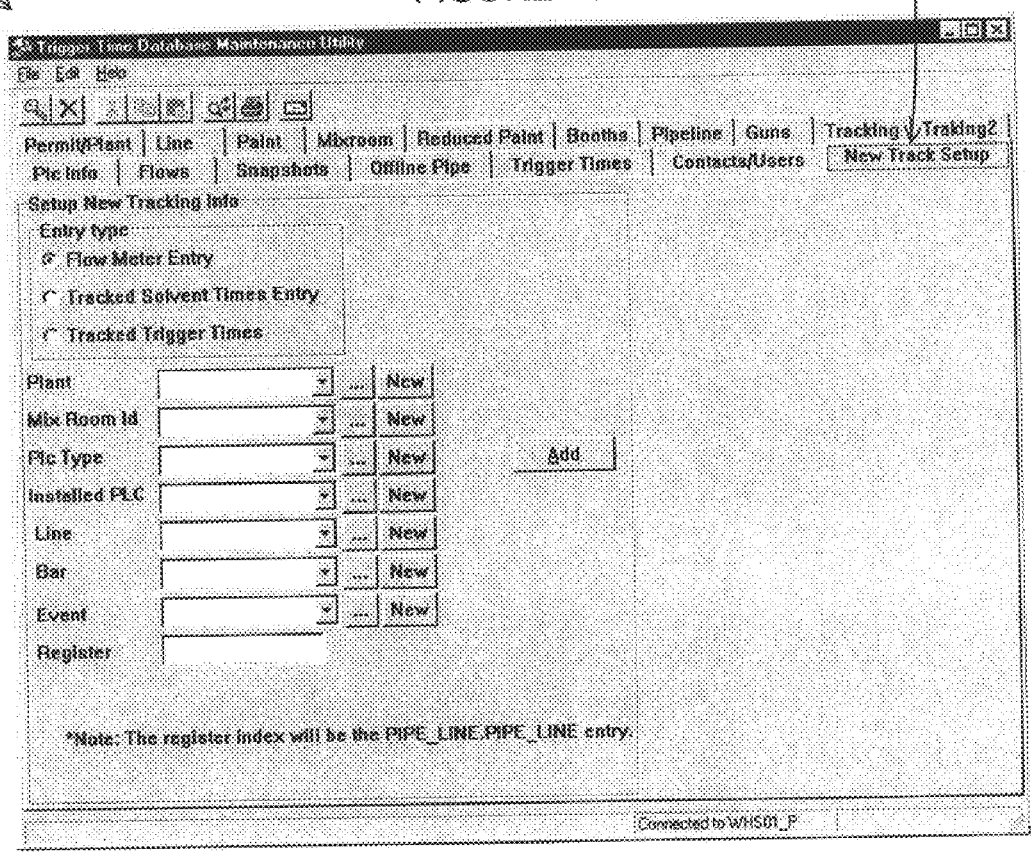
FIG. 10P is a user interface showing tracking setup information and intended for interaction with an operator via a computing device according to another exemplary embodiment.
Figure 10Q:
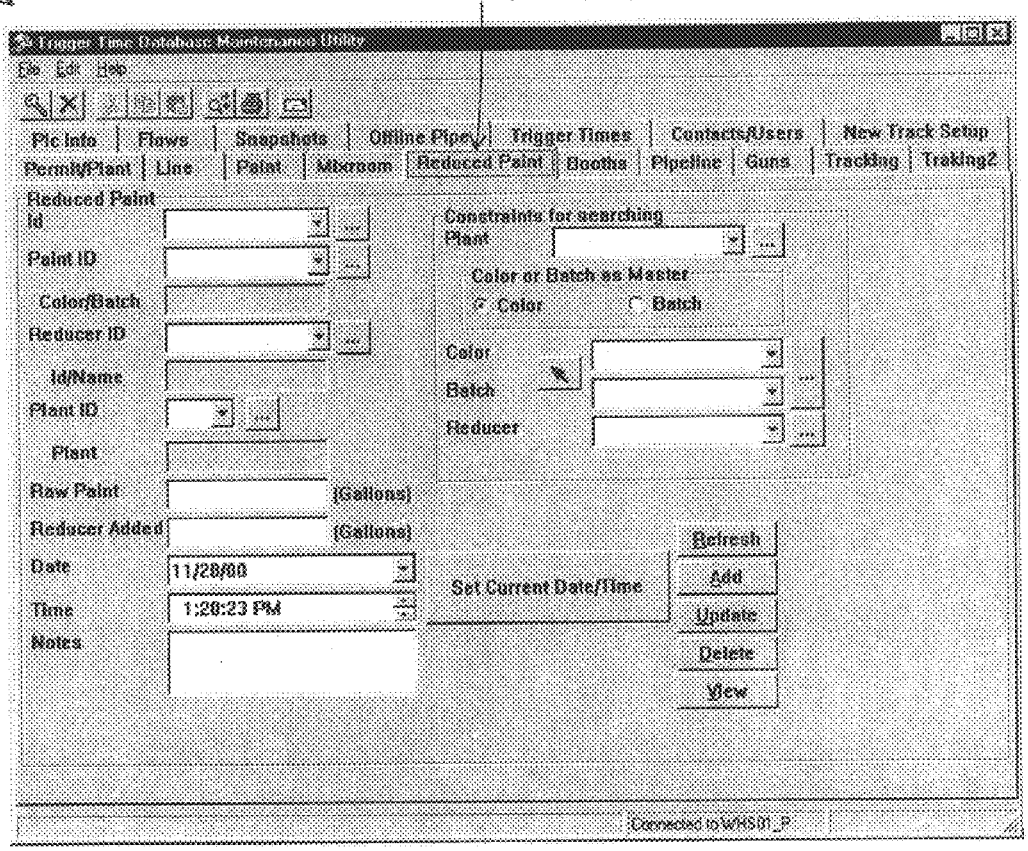
FIG. 10Q is a user interface showing reduced paint information and intended for interaction with an operator via a computing device according to an exemplary embodiment.

User interfaces 340a through 340q are shown in FIGS. 10A through 10Q. User interfaces 340a through 340q are suited for use by administrator 190 to manipulate values in database 174a. According to a preferred embodiment, the user interface is a Borland C++ Builder software program commercially available from Borland International, Inc. of Scotts Valley, Calif. According to an alternative embodiment, users may manipulate the values in the database through other interfaces. According to another alternative embodiment, the user interface may be customized to suit the purposes of a particular user (e.g., supervisor, mix room operator, off-line operator, administrator, lab technician, end user, etc.).

Referring to FIG. 10A, user interface 340a related to permit information is shown. Interface 340 includes a title bar 342a (e.g., a VOC monitoring system database maintenance utility bar). Title bar 342a includes buttons or icons 344a to minimize, restore, close the size of interface 340 on a computer screen. A file menu 346a (e.g., file, edit, options, preferences, tools, format, insert, window, etc.) is positioned below title bar 342a. File menu 346a includes drop down file items according to a preferred embodiment as shown in FIGS. 10A through 10Q. User interfaces 340a through 340g also include title bar 342a and file menu 346a.

A button or icon bar 348 is located below file menu 346a. Icon bar 348 provides buttons or icons 350 for quick access to the drop down file items. Icons 350 serve various functions including, deleting, cutting, saving to a clipboard, pasting, enlarging and reducing, mailing, etc. according to alternative embodiments as shown in FIGS. 10A through 10Q. A status bar 352 (e.g., identifying a connection to "WHSO1_D") is located at the bottom of interface 340 to show the status of information (e.g., network connection, time, etc.)

Interface 340 includes tabs or folders (shown as a folder 354a in FIG. 10A) for organization of information. Each of the folders is directed to a different aspect of data value collection in monitoring system 100a. Each of the folders includes a data entry field 356a for manipulation of data values, and a selection field 388 (for performing an action, e.g., "refresh" to re-read data values in a data field, "add" to add a record to the database, "update" to change a record, "delete" to expunge or remove a record, "view" to bring up a spreadsheet view of a table, "drill" to access data values associated with a field such as all installed PLCs for a plant) on the data values in the data fields. Data values may be selected manually (e.g., by keying in from an input device such as a keyboard), from a menu (shown as a drop down menu 362) or automatically (e.g., input from an input device or sensor). Each of the folders may be separated into modules for categorizing information (shown as modules 360a and 360b in FIG. 10A). Each module is generally associated with table 230 in database 174a. Data entry fields 356a are associated with the data fields shown in table 230 of FIG. 9A. Data values 366 (e.g., shown as "Sep. 19, 2000" in FIG. 10A) are input into data entry fields 356a of user interface 340, which are transferred to database 174a.

The user interface may be web or Internet-based according to alternative embodiments. The user interface may have a highly ornamental appearance according to other alternative embodiments. The user interfaces may be customized for manipulation of the data values according to alternative embodiments. For example, the user interface may be limited to the display of data entry fields that are only relevant to a particular user (e.g., color and batch information displayed for a spray gun operator). Such customization of the user interface assists in restricting access by certain personnel to sensitive data, which also provides increased integrity to the data values in the database. The user interface may also implement user permissions or restrictions to provide access to the particular data values needed by a particular user and to restrict access to the data values by others who do not require such-access. For example, the mix room operator has access to the mix room folder, and the lab technician has access to the paint folder (not necessarily vice-versa) according to a preferred embodiment.

Folder 354a related to permit and plant information is shown in FIG. 10A. Module 360a of folder 354a is related to table 264 for input of data values relating to plant operating times into the data fields of table 268. Module 360b of folder 354a is related to table 262 showing plant information for input of data values into the fields of table 262. Module 360a of folder 354a is associated with table 268 for input of data values relating to plant operating times into the data fields of table 268. Module 360d of folder 354a is associated with table 266 for input of data values relating to permit and plant information into the data fields of table 266.

A folder 354b related to paint information is shown in FIG. 10B. Module 360e of folder 354b is associated with table 272 for input of data values relating to supplier information into the data fields of table 272. Module 360f of folder 354b is associated with table 232 for input of data values relating to paint information into the data fields of table 232. Module 360g of folder 354b is associated with table 270 for input of data values relating to reducer information into the data fields of table 270.

A folder 354c related to mix room information is shown in FIG. 10C. The data entry fields of folder 354c are associated with the data fields of table 280 for input of data values relating to mix room information. A folder 354d related line information is shown in FIG. 10D. Module 360h of folder 354d is associated with table 282 for input of data values relating to line information into the data fields of table 282. Module 360i of folder 354d is associated with table 250 for input of data values relating to line operating times information into the data fields of table 250.

A folder 354e related to pipeline information is shown in FIG. 10E. Module 360j of folder 354e is associated with table 248 for input of data values relating to pipeline information into the data fields of table 248. Module 360k of folder 354e is associated with table 246 for input of data values relating to pipeline history information into the data fields of table 246.

A folder 354f related to booth information is shown in FIG. 10F. Module 360d of folder 354f is associated with table 292 for input of data values relating to booth information into the data fields of table 292. Module 360m of folder 354f is associated with table 290 for input of data values relating to bar information into the data fields of table 290. A folder 354g related to offline information is shown in FIG. 10G. Folder 354g is associated with table 240 for input of data values relating to offline information into the data fields of 240 table.

A folder 354h related to gun information is shown in FIG. 10H. Module 360n of folder 354h is associated with table 300 for input of data values relating to gun type information into the data fields of table 300. Module 360o of folder 354h is associated with table 298 for input of data values relating to gun type information into the data fields of table 298. Module 360p of folder 354f is associated with table 296 for input of data values relating to event information into the data fields of table 296. Module 360q of folder 354h is associated with table 294 for input of data values relating to event information into the data fields of table 294. A folder 354i related to trigger time information is shown in FIG. 10I. Module 360r of folder 354i is associated with table 236 for input of data values relating to trigger time information into the data fields of table 236. Module 360s of folder 354i is included in interface 340j.

A folder 354j related to PLC information is shown in FIG. 10J. Module 360t of folder 354j is associated with table 302 for input of data values relating to PLC type information into the data fields of table 302. Module 360u of folder 354j is associated with table 306 for input of data values relating to installed PLC information into the data fields of table 306. Module 360v of folder 354j is associated with table 304 for input of data values relating to PLC available registers information into the data fields of table 304.

A folder 354k related to tracking information is shown in FIG. 10K. Module 360w of folder 354k is associated with table 308 for input of data values relating to tracked register information into the data fields of table 308. Module 360x of folder 354k is associated with table 234 for input of data values relating to tracked flow information into the data fields of table 234. Module 360y of folder 354k is associated with table 312 for input of data values relating to tracked trigger time information into the data fields of table 312. Module 360z of folder 354k is associated with table 314 for input of data values relating to tracked solvent time information into the data fields of table 314.

A folder 354l related to additional tracking information is shown in FIG. 10L. Module 370a of folder 354l is associated with table 286 for input of data values relating to tracked plant operating time information into the data fields of table 286. Module 370b of folder 354l is associated with table 288 for input of data values relating to tracked line operating time information into the data fields of table 288. Module 370c of folder 354l is associated with table 284 for input of data values relating to interface register information into the data fields of table 284.

A folder 354m related to flow information is shown in FIG. 10M. Module 360d of folder 354m is associated with table 310 for input of data values relating to flow information into the data fields of table 310. Module 360e of folder 354m is associated with table 238 for input of data values relating to flow amount information into the data fields of table 238.

A folder 354n related to snapshot information is shown in FIG. 10N. Module 360f of folder 354n is associated with table 252 for input of data values relating to PLC snapshot information into the data fields of table 252. Module 360g of folder 354n is associated with table 254 for input of data values relating to PLC snapshot register information into the data fields of table 254. The snapshot of the PLC registers may collect all data values in the PLC, although not all the data values may be needed for database 174a.

Referring to FIG. 10O, a folder 354a related to contact and user information is shown. Folder 354a relates to information to be input into the data fields of contact view 254 of database 174a shown in FIG. 9B. Module 370f of folder 354o is shown having data entry fields for input of information related to users. A folder 354p related to new tracking information is shown in FIG. 10P. Information related to additional plants, mix rooms, PLCs, lines, bars, events, registers, etc. may be input into the data entry fields of folder 354p. A folder 354q related to reduced paint information is shown in FIG. 10Q. Folder 354q is associated with table 316 for input of data values relating to reduced paint information into the data fields of table 316.

Figure 11A:
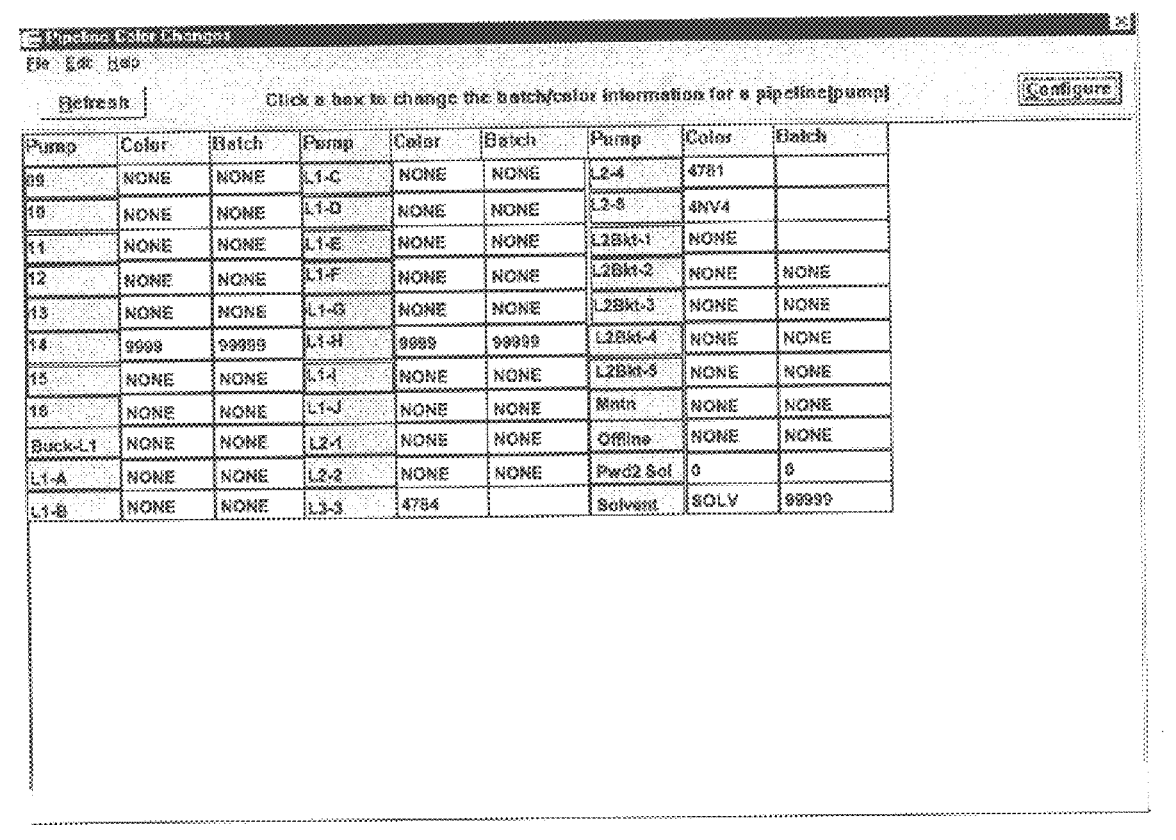
Figure 11B:
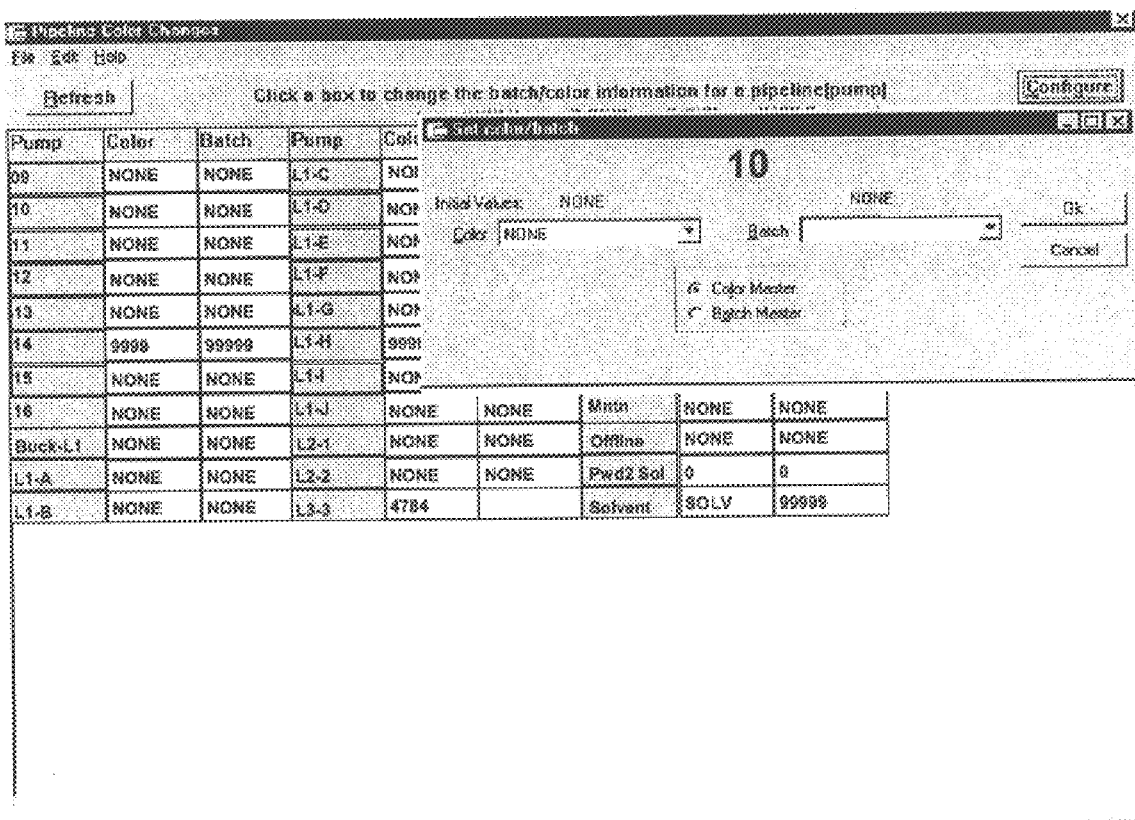
FIG. 11B is a user interface showing pipeline master color and master batch information and intended for interaction with an operator via a computing device according to an exemplary embodiment.

Additional user interfaces are shown in FIGS. 11A and 11B. User interfaces 380 and 382 are suited for use by a shop floor user to manipulate (i.e., input and monitor) data values in local database 174c. Interface 380 and interface 382 are intended to communicate to the database what coating (e.g., color and batch) is discharged from each gun for a particular period. Such information permits end user 186 to monitor VOC emissions at various levels of the enterprise.

Referring to FIG. 11A, user interface 380 intended for use on the shop floor and related to pipeline color changes is shown. Interface 380 includes a title bar 342b (e.g., a pipeline color change bar). Title bar 342b includes buttons or icons 344b to minimize, restore, close the size of interface 380 on a computer screen. A file menu 346b (e.g., file, edit, options, preferences, tools, format, insert, window, etc.) is positioned below title bar 342b. File menu 346b includes drop down file items according to a preferred embodiment as shown in FIG. 11A.

Interface 380 is intended to restrict the amount of information that is available from local database 174c and corporate database 174b to a user. Specifically, interface 380 shows data entry fields 356b arranged as columns relating to pump, color and batch information. Referring to FIG. 11B, user interface 382 may be accessed by selecting a "pump" button (e.g. pump 10). Interface 382 shows that color and batch information may be selected or set from a master set of values (e.g., color master, batch master, etc.) set by computing device 172b shop floor. Access is restricted or "locked down" so a user may select only predetermined data for entry into data entry fields 356b).

Figure 11D:
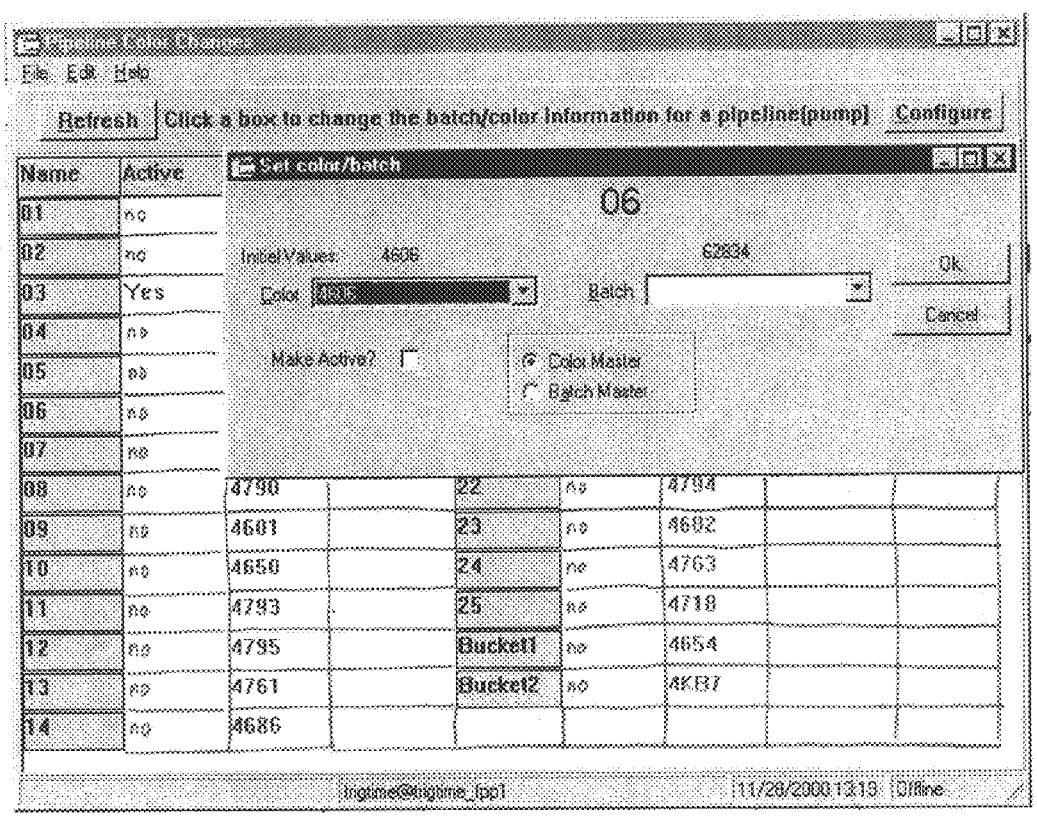
FIG. 11D is a user interface showing pipeline color change information and intended for interaction with an operator via a computing device according to an exemplary embodiment.
Figure 11E:
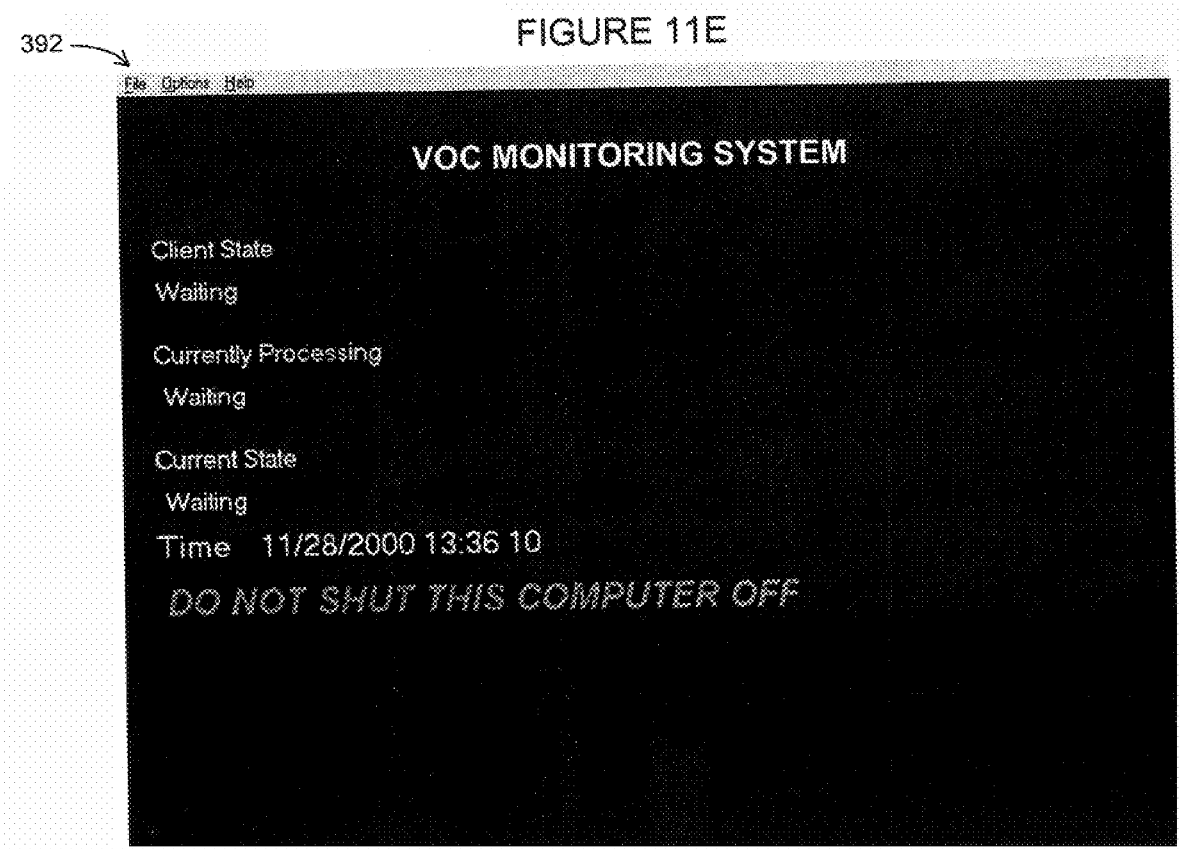
FIG. 11E is a user interface showing transition information and intended for interaction with an operator according to an exemplary embodiment.

A user interface 384 is shown in FIG. 11C. Interface 384 is intended for use on the shop floor of an off-line workstation. Interface 384 is provided by computing device 172c. Interface 386 has similar fields as interface 380, and also indicates whether a particular pump is "active" or engaged. Interface 386, similar to interface 382, is shown in FIG. 11D. A worker in an off-line workstation uses interface 386 to select the color and batch of coating to be applied in the off-line workstation. A default interface 392 is shown in FIG. 11E. Interface 392 is used as a transition interface in association with user interfaces 380 through 388.

Figure 12:
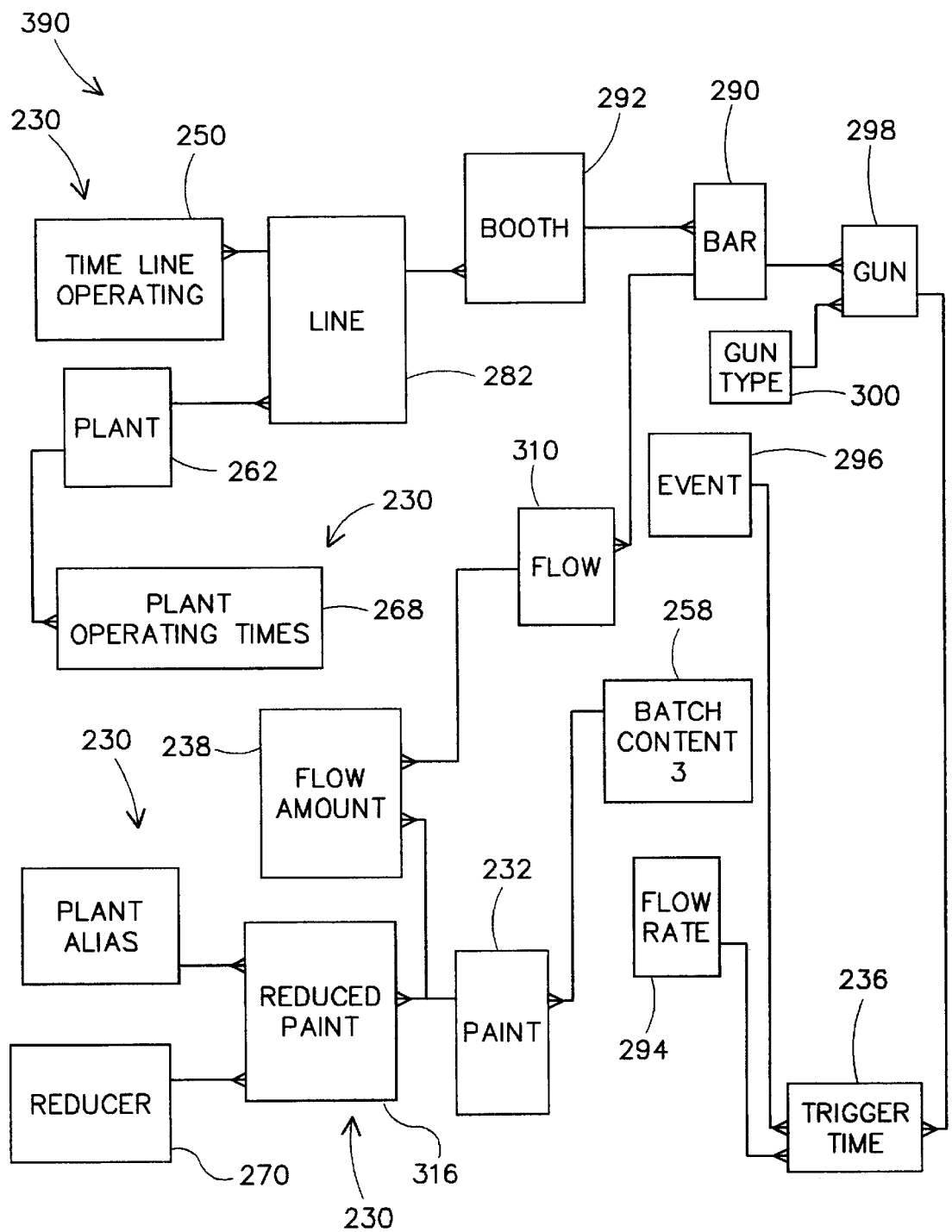
FIG. 12 is a block diagram of a database universe according to a preferred embodiment.

A database universe or access path 390, a subset of global database 200, is shown in FIG. 12. Universe 390 includes related tables 230 and provides a path or map to the data fields of database 200. The tables (e.g., tables 292 and 290) are arranged in a "one to many" relationship. For example, one booth may have multiple bars, and one bar may have multiple guns (see for example tables 292, 290 and 298 in FIG. 12).

Universe 390 is useful for arranging the data values necessary to generate a report representative of the data values (see FIGS. 14A through 14G). For example, table 268a and table 242 shown in FIG. 12 are each "mapped" to collect information from table 268 in global database 200. The data values used to generate the reports are accessed by end user 186 through a user interface 400. According to a particularly preferred embodiment, the database universe is a Business Objects access path commercially available from Business Objects, S.A. of Paris, France.

Figure 13A:
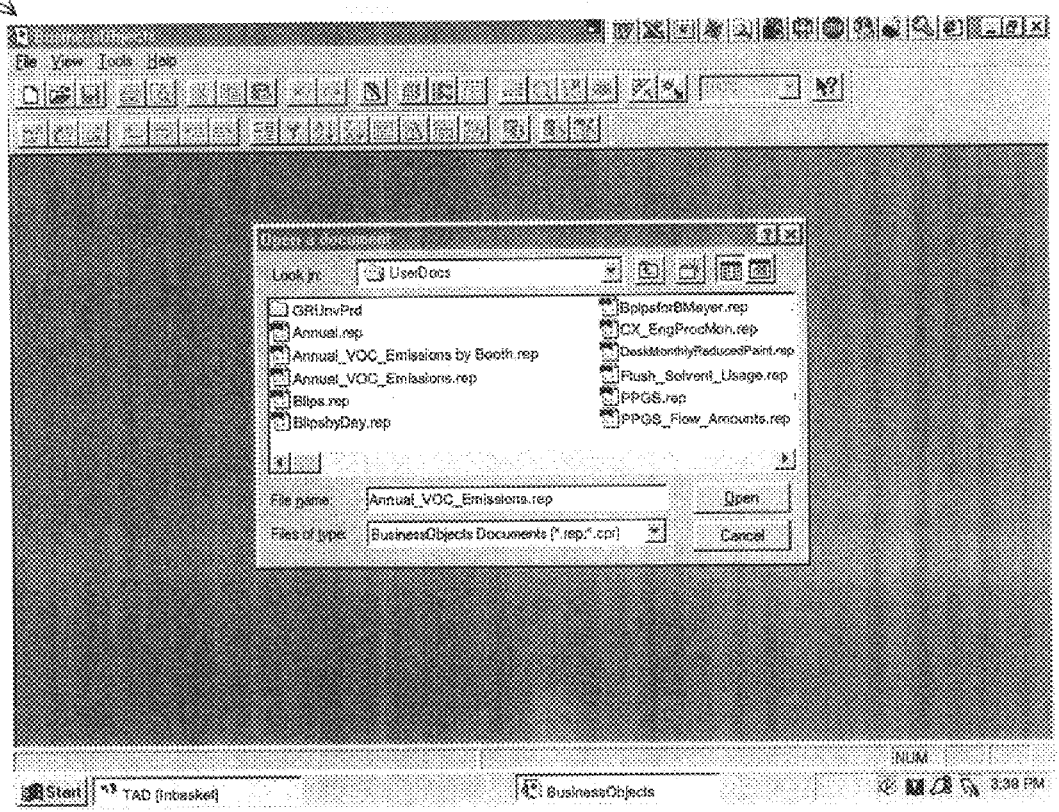
FIG. 13A is a user interface showing report information and intended for interaction with an operator via a computing device according to an exemplary embodiment.
Figure 13B:
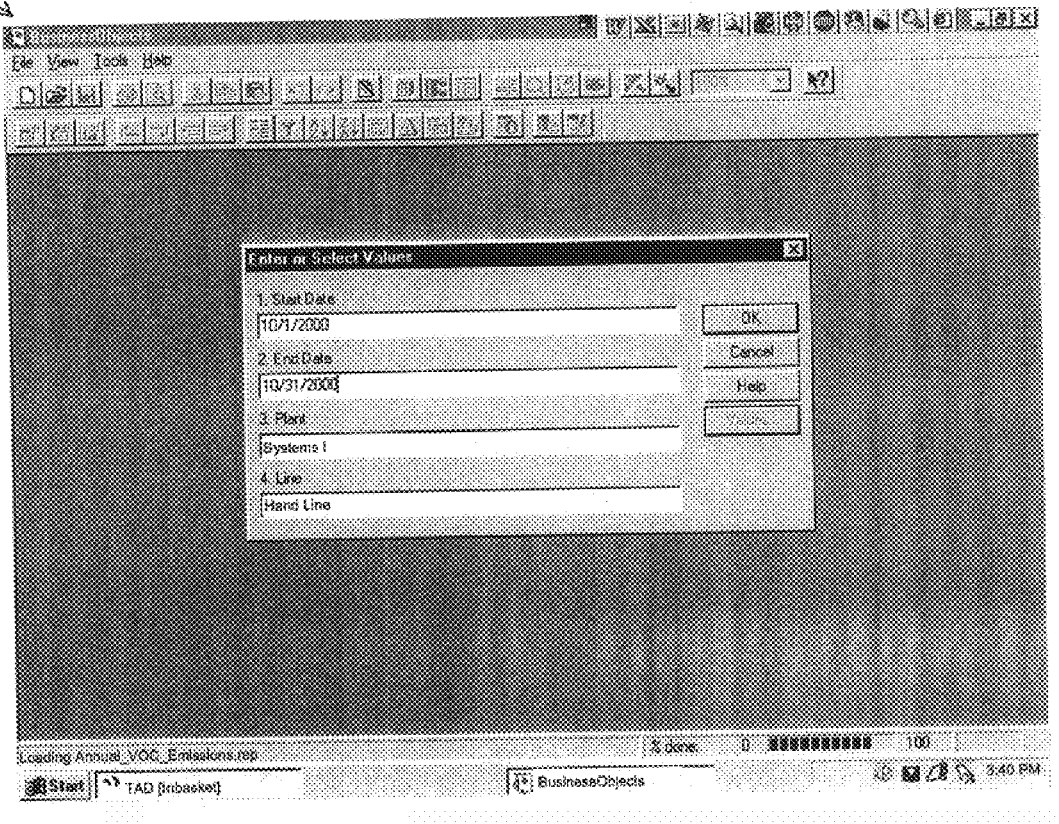
FIG. 13B is a user interface showing report parameter information and intended for interaction with an operator via a computing device according to another exemplary embodiment.

Referring to FIG. 13A, user interface 400 for selecting a type of report to be generated is shown. User interface 400 enables end user 186 to manipulate (e.g., share) a wealth of information stored in database 174a and allows the generation of reports. Manipulation of such information provides end user 186 with autonomous access to the data values used for decision making. End user 186 may select from a variety of reports to be generated (e.g., annual report, annual VOC emissions for enterprise, annual VOC emissions by booth, PPGS by trigger times, PPGS by flow amounts, flush solvent usage, flush or blips by period (e.g., month), flush or blips by day, etc.). After selecting the type of report to be generated, the user may select a parameter from a subsequent user interface 402. Such parameters include, for example, start date, end date, plant, line, etc. according to an exemplary embodiment as shown in FIG. 13B. According to a particularly preferred embodiment, the user interface and associated software is a customized Business Objects user interface commercially available from Business Objects, S.A. of Paris, France. According to an alternative embodiment, the user interface and associated software may be Crystal Reports software commercially available from Seagate Software Incorporated of Scotts Valley, Calif. The user interface includes a title bar, menu bar, sizing bar, icon bar and status bar as shown in FIGS. 13A and 13B.

Such reports may be used by administrator 190 for audits or monitoring of database 174a. The reports may be customized to suit the needs of a particular user at any level in the enterprise (including executive management and other persons associated with the enterprise who are given permission or authorization). A suitable report shows the relevant information required by a user. For example, the reports may notify the administrator of an escalation in VOC emissions or the impact of a failure. An indication of failure may be useful for determining if a workpiece should be discontinued or "pulled" due to problems with the coating. The reports may also be used to cross check data values. For example, a report may indicate the amount in gallons of each color paint sprayed (and reducer) during a month (e.g., month) based on computing device 172b in mix room 108a information check against the amount of each paint sprayed as determined by using the average gun flow rate and gun operating time information from computing device 172a on the shop floor. According to an alternative embodiment, all or selected data values in the database may be generated in a report. According to a preferred embodiment, the report may indicate a calculated value performed on the data values in the database.

Figure 13C:
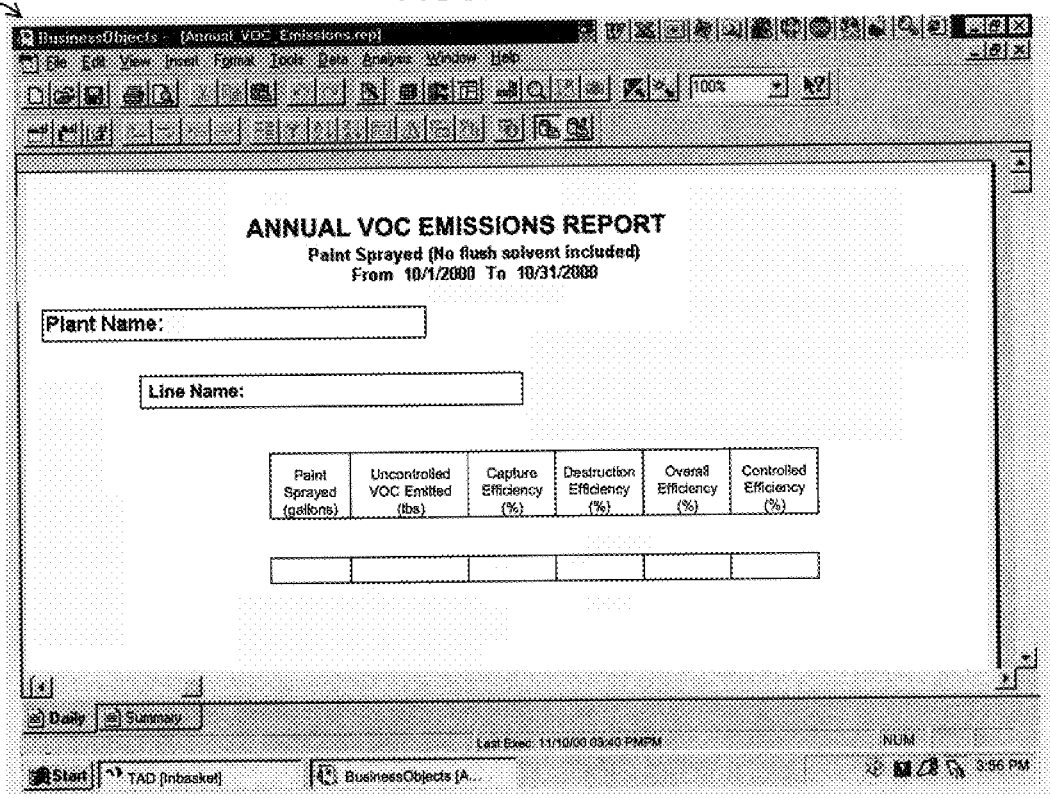
FIG. 13C is a user interface showing a report according to an exemplary embodiment.

The reports may also be used for a variety of environmental, accounting and production purposes, and may be generated for data values accumulated over any period. An exemplary report 404 of VOC emissions is shown in FIG. 13C. Report 404 can indicate the concrete, tangible and useful result of controlled VOC emitted in pounds for a particular line (e.g., hand line, automated line, offline, etc.) of a particular plant (e.g., plant, furniture plant, casegoods plant, etc.) over a particular period (e.g., the month of October, 2000, annually, hourly, etc.). Report 404 can include the combined VOC emissions from coating discharge (step 514 in FIG. 4) and purge coating (step 516). Reports may be generated on the screen of a computing device according to an exemplary embodiment as shown in FIG. 13C, and may be generated with other information and using other formats (shown in FIG. 14A as a report 410 according to an alternative embodiment). According to an alternative embodiment, the report can include VOC emissions data related to a particular workstation or spray gun, and can show VOC emissions from flush solvent (step 522 in FIG. 4) as shown in FIG. 14E. Specific values are not necessarily shown in each field of the reports. Exemplary data may be identified in the fields of the report as would be understood by one of skill who reviews this disclosure.

A report 412 directed to PPGS flow meters also produces a concrete, useful tangible result of the pounds of VOC per Gallon of coating solids as applied as shown in FIG. 14B. PPGS report 416 may be generated using data values from flow meters as shown in FIG. 14C according to an alternative embodiment where narrow guidelines and close precision is required. The PPGS report may also be generated using a data values from trigger times according to a preferred embodiment (shown as report 412 directed to PPGS in FIG. 14B).

The report may also indicate how much coating is applied during a particular period for each color and batch (as shown in report 418 directed to surface coating usage in FIG. 14D). The report may also indicate how much solvent was spent during flushing of the line (step 520 in FIG. 4) for a particular line, and the VOCs emitted corresponding to the flush solvent, as shown in a report 420 directed to flush solvent usage in FIG. 14E. According to an alternative embodiment, a report on VOC content as applied may be generated. A report 422 showing line operating times may be generated as shown in FIG. 14F, and a report 424 showing blip or flush time may be generated as shown in FIG. 14G. Report 424 showing flush time is useful to determine if a PLC is operating properly (e.g., a report of a relatively high flush time may indicate that a PLC register has not been properly reset).

A variety of reports based on data in the corporate database may be generated according to alternative embodiments. Batch vs. Supplier information reports may be generated. Batch vs. MSDS information reports may be generated which compare the pounds of VOC per gallon of raw and reduced paint to values provided by the paint suppliers in their MSDS and batch paint VOC information report. The batch vs. MSDS information reports may also track paints and suppliers with pound per gallons reduced paint VOC levels that exceed a particular threshold value (e.g., 2.79 lb. VOC/gal., 7.51 lbs. VOC/gallon, etc). A batch vs. MSDS pounds VOC per gallon (raw) report may be generated. The batch vs. MSDS pounds VOC per gallon (raw) report may compares the VOC content of the raw paint as received by the paint supplier against the typical VOC content of the paint as stated in the raw paint MSDS. A batch vs. supplier pounds VOC per gallon (reduced) report may be generated. The batch vs. supplier pounds VOC per gallon (reduced) report may compare the VOC content of the paint as reduced by personnel in the mix room, to the supplier estimated reduced paint VOC content. A high batch pounds VOC per gallons (reduced) report may be generated. The high batch pounds VOC per gallon (reduced) report may list all of the paint batches that fail to meet a particular standard (e.g., 2.79 lbs. VOC/gallon of reduced paint).

A variety of reports related to finishing data values may be generated. The amount of coating usage by plant, line, booth or workstation may be generated. Likewise, the amount of coating (e.g., solids and solvent) flushed (steps 520 and 522 in FIG. 4) may be generated for each plant, line, and workstation. The amount of coating used in the mix room may also be generated to assist in maintaining inventory (e.g., just in time inventory control) according to an alternative embodiment.

A variety of air quality reports may be generated according to alternative embodiments. The reports may be customized to be suitable for periodic reporting to government agencies. Such air quality reports may be related to VOC content, VOC contents by line, pre-reduced paint batches, Michigan Rule 610 report, hourly/daily VOC emissions. The reports may be customized to indicate any of the information contained in the database. According to other alternative embodiments, the reports may include system information reports, paint mix room reduction reports, paint mix room usage report, trigger time data reports, operating times reports, supplier reported VOC reports, MAPR reports, paint shop information reports, plant reduced paint summary reports, paint and solvent wasted per change reports, plant solvent reports, database management reports, etc.

In general, the pounds of VOC per gallon of coating solids as applied can be calculated for a report by multiplying the trigger time (seconds) by the flow rate through the spray gun. (The flow rate may depend on factors such as the gun type and mode of operation (e.g., spray, blip, flush, etc.) According to an alternative embodiment, PPGS may be calculated by determining the amount of spray using a flow meter. The total VOC emissions due to coating can be determined by summing the emissions due to coating discharge (step 514), flush coating (step 520) and flush solvent (step 522).

VOC emissions (e.g., annual) are calculated as follows according to a preferred embodiment using the following "pseudo code" or logic:

controlled VOC emitted (tons)=(uncontrolled VOC emitted*(1−overall control efficiency))/tons where: overall control efficiency=capture efficiency+destruction efficiency.

The transfer efficiency is related to the percentage solids caught by a filter. Hourly VOC emissions may be calculated according to an alternative embodiment using "pseudo code" or logic:

controlled VOC (lbs./hour)=(uncontrolled VOC emitted*(1−overall control efficiency))/daily operating hours where: overall control efficiency=capture efficiency+destruction efficiency.

Pounds of VOC per gallon of coating solids as applied (controlled ppgs) are calculated according to a preferred embodiment using the following "pseudo code" or logic:

controlled ppgs=(uncontrolled VOC emitted*(1−overall control efficiency))/(coating solids*volume weighted transfer efficiency).

where: overall control efficiency=capture efficiency+destruction efficiency.

VOC content, as applied is calculated according to the following equation:

controlled VOC content as applied=(uncontrolled VOC emitted*(1−overall control efficiency))/(paint sprayed)

where: overall control efficiency=capture efficiency+destruction efficiency.

The surface coating usage is calculated by the following equation:

total paint sprayed=raw paint sprayed+solvent sprayed.

According to an alternative embodiment, overall VOC emissions may be calculated according to the following equations:

1) Pounds of VOC per gallon, reduced:

$$E = \sum_{additions} \frac{A \times B + C \times D}{A + C}$$

2) Paint Application VOC:

$$Paint\ Application\ VOC = \sum_{line} \sum_{gun} \sum_{batch} F \times E \times (1 - (CE * DE))$$

3) Paint Blip VOC:

$$Paint\ Blip\ VOC = \sum_{line} \sum_{gun} \sum_{batch} Q \times E \times (1 - (CE * DE))$$

4) Solvent Blip VOC:

$$Solvent\ Blip\ VOC = \sum_{line} \sum_{gun} R \times D \times (1 - (CE * DE))$$

5) Overall VOC Emissions:

Overall VOC Emissions=Paint Application VOC+Coating Purge VOC+Solvent Purge VOC where:
A=gallons of coating, as received
B=pounds of VOC per gallon of coating, as received
C=gallons of reducer
D=pounds of VOC per gallon of reducer
E=pounds of VOC per gallon of coating, reduced
F=reduced paint sprayed, gallons
Q=paint purged, gallons
R=reducer purged, gallons
CE=line capture efficiency
DE=line destruction efficiency
TE=gun transfer efficiency.

Flush solvent usage is calculated by determining the amount of solvent discharged using VOC monitoring systems or flow meters.

A software program performs regulatory calculations on the data values in the database. Such calculations are typically outlined by a statute or agency rule, and include New Source Performance Standards Calculations (40 C.F.R. §§ 60.310–60.316), Michigan Rule 610 Calculations (e.g. Michigan Rule 336.1601–336.1702), Volatile organic compound (VOC) Emission Calculations, Particulate Emission Calculations, VOC emission units (lbs VOC) over time under Michigan Rule 290 (Michigan Rule 336.1290), and VOC emission units overtime (gallons VOC) under Michigan Rule 287c (Michigan Rule 336.1287(c)), and Hazardous Air Pollutant (HAP) Emission Calculations. The calculations may produce a useful, concrete tangible result of a data value that is useful for periodic governmental reporting requirements.

Volume weighted average of the total mass of VOCs consumed per unit volume of coating solids applied during each calendar month for each line may be calculated based on 40 C.F.R. § 60.313 subpart EE titled "Standards of Performance for Surface Coating of Metal Furniture." The Total Mass of VOCs used during each calendar month may be calculated based on 60 C.F.R. § 313(c)(i)(A) according to an alternative embodiment, which states:

$$M_o + M_d = \sum_{i=1}^{n} L_{ci} D_{ci} W_{oi} + \sum_{j=1}^{m} L_{dj} D_{dj}$$

where:
$M_o$=the mass of VOCs in coatings consumed, as received
$M_d$=the mass of diluent VOC-solvent consumed
$L_c$=the volume of each coating consumed, as received
$D_c$=the density of each coating as received
$W_o$=the proportion of VOCs in each coating as received
$L_d$=the volume of each diluent consumed, as received $D_d$=the density of each diluent consumed n=the number of different coatings used during the calendar month m=the number of different diluent VOC-solvents used during the calendar month.

The total volume of coating solids used during each calendar month may be calculated based on 60 C.F.R. § 313(c)(1)(i)(b) according to an alternative embodiment, which states:

$$L_s = \sum_{i=1}^{n} L_{ci} V_{si}$$

where:

$L_s$=the volume of coating solids consumed $L_{ci}$=the volume of each coating consumed $V_{si}$=the proportion of solids in each coating, as received (fraction by volume)

n=the number of different coatings used during the calendar month.

The volume weighted average mass of VOCs consumed per unit volume of coating solids applied during the calendar month may be calculated based on 60 C.F.R. § 313(c)(1)(i)(B) according to an alternative embodiment, which states:

$$G = \frac{M_o + M_d}{L_s T}$$

where:

G=the volume-weighted average mass of VOCs in coatings consumed in a calendar month per unit volume of coating solids applied $M_o$=the mass of VOCs in coatings consumed, as received $M_d$=the mass of diluent VOC-solvent consumed $L_s$=the volume of coating solids consumed T=the transfer efficiency (fraction).

The volume weighted average of VOC emissions to the atmosphere during the calendar month may calculated based on 60 C.F.R. § 313(c)(1)(i)(C)(iii) according to an alternative embodiment, which states:

$$N = G(1-R)$$

where:

N=the volume weighted average mass of VOC emissions to the atmosphere per unit volume of coating solids applied G=the volume weighted average mass of VOCs in coatings consumed in a calendar month per unit volume of coating solids applied R=the overall VOC emission reduction achieved for an affected facility.

According to another alternative embodiment, the volume weighted average pounds of volatile organic compound emitted per gallon of coating, minus water, as applied for each line may be calculated based on Michigan Rule 336.2040(12)(a) for lines that do not have an add-on emissions control device, and R336.2040(12)(b) for lines that have add-on emission control devices.

The VOC content of each coating used on a line may be based on Michigan Rule 336.2040(12)(a)(A) and Michigan Rule 336.2040(12)(b)(B) according to an alternative embodiment. VOC information may be obtained from suppliers for every batch of paint that is sprayed. This information may be used along with MSDS VOC information for the reducers to calculate pounds of VOC per gallon for each batch of paint. Pounds of VOC per gallon of reduced coating may be calculated by the following equation:

$$\text{Pounds of VOC per gallon of reduced coating } (E) = \sum_{i=1}^{z} \frac{A_i \times B + C_i \times D}{A_i + C_i}$$

where:

A=gallons of coating, as received

B=pounds of VOC per gallon of coating, as received

C=gallons of reducer

D=pounds of VOC per gallons of reducer z=number of additions to the batch.

The weight or mass of volatile organic compounds that are used during the day may be calculated based on Michigan Rules 336.2040(12)(a)(B) and 336.2040(b)(C) according to an alternative embodiment, which states:

$$M = \sum_{i=1}^{z} L_{ci} P$$

where:

M=total weight of volatile organic compounds in all coatings "z" used during the day $L_{ci}$=volume of each coating used during the day P=pounds of volatile organic compounds per gallon of coating, minus water, as applied.

The total volume of coatings used on the line during the day may be based on Michigan Rules 336.2040(12)(a)(C) according to an alternative embodiment, which states:

$$G_T = \sum_{i=1}^{z} L_{ci}$$

where:

$G_T$=total volume of all coatings "z" used during the day $L_{ci}$=volume of each coating used during the day.

The total volume of coating solids that are used during the day may be based on Michigan Rule 336.2040(12)(b)(D) according to an alternative embodiment, which states:

$$V = \sum_{i=1}^{z} L_{ci} V_{ci}$$

where:

V=the volume of solids in all coatings used during the day (gallons)

$L_{ci}$=volume of each coating used during the day.

The volume weighed average weight of volatile organic compounds per gallon, minus water, as applied may be based on Michigan Rule 336.2040(12)(a)(D) according to an alternative embodiment, which states:

$$Pa = \frac{M}{G_T}$$

where:

M=total weight of volatile organic compounds in all coatings "z" used during the day $G_T$=total volume of all coatings "z" used during the day $P_a$=volume weighed average pounds of volatile organic compounds per gallon of coating, minus water, as applied for a single coating category during the day.

The volume weighted average weight of volatile organic compounds per gallon of coating solids, as applied, may be calculated based on Michigan Rule 336.2040(12)(b)(G) according to an alternative embodiment, which states:

$$P_b = \frac{M}{V}(1 - R_T)$$

where:

$M$=total weight of volatile organic compounds in all coatings "z" used during the day $V$=the volume of solids in all coatings used during the day (gallons)

$R_T$=overall reduction efficiency of all ad-on emissions control devices used for a line $P_b$=Volume weighted average pounds of volatile organic compounds per gallon of coating, minus water, as applied for a single coating category during the averaging period.

Other calculation may be performed according to alternative embodiments to determine, for example, total mass of VOCs, total volume of coating solids, the volume-weighted average mass of VOCs per volume coating solids, the volume weighted average of VOC emissions to the atmosphere, etc.

It is important to note that the terms "channel" is not meant as terms of limitation, insofar as the structures described in this specification (or alternative and/or equivalent structures) may serve to provide for the flow of a fluid through a passage, chamber, tube, conduit, inlet, intake, outlet, discharge, port, pipe, channel, etc.

It is important to note that the term "article of furniture" is intended to be a broad term and not a term of limitation. Article of furniture, as used in this disclosure, may include, without limitation: systems furniture (e.g., partition wall systems, architectural walls, space frames, work stations, etc.), casegoods (e.g., file cabinets, storage bins, containers, closets, etc.), seating products (e.g., chairs, stools, lounges, etc.), worksurfaces (e.g., tables, desk systems, credenzas, etc.), lighting systems, and other accessories.

It is also important to note that the construction and arrangement of the elements of the monitoring system as shown in the preferred and other exemplary embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. According to an alternative embodiment, the monitoring system may be configured to determine powder coating usage and emission information (e.g., mass balance correlated) for use in electrostatic coating operations. The monitoring system could be implemented on a wide variety of computing platforms using a wide variety of database or software programs according to alternative embodiments. The data values may be collected in a single database, multiple databases, distributed (e.g., over a network) databases, etc. The system may be "Y2K compliant" according to an alternative embodiment. The data values may be contained in one or more databases according to alternative embodiments. Accordingly, all such modifications are intended to be included within the scope of the present invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the preferred and other exemplary embodiments without departing from the spirit of the present inventions as expressed in the appended claims.

What is claimed is:

1. A system for monitoring the emission of volatile organic compounds in a workstation comprising:

a sensor configured to obtain a signal representative of an amount of a coating discharged in the workstation;

a local database configured to store data values representative of the coating;

a corporate database configured to retrieve the data values from the local database;

a network configured to permit manipulation of the data values in the corporate database;

wherein the coating comprises a surface finish.

2. The system of claim 1 wherein the manipulation includes adding the data values.

3. The system of claim 1 wherein the manipulation includes changing the data values.

4. The system of claim 1 wherein the manipulation includes presenting information representative of at least a portion of the data values.

5. The system of claim 1 further comprising a user interface for presenting information representative of at least a portion of the data values over the network.

6. A method of monitoring the emission of volatile organic compounds in a workstation comprising:

measuring a signal representative of an amount of a coating discharged in the workstation;

storing in a database a first data value representative of an amount of the coating discharged in the workstation;

inputting a second data value representative of the coating in the database;

accessing the database over a network to generate a report representative of the first data value and the second data value;

wherein the coating comprises a finish.

7. The method of claim 6 further comprising modifying at least one of the first data value and the second data value in the database.

8. The method of claim 7 further comprising generating a report of volatile organic compounds emitted in the workstation.

9. The method of claim 6 further comprising presenting information representative of the first data value and the second data value at a user interface.

10. The method of claim 6 further comprising presenting information representative of the first data value and the second data value in a report.

11. A system for monitoring the emission of volatile organic compounds in a workstation comprising:

a sensor to obtain a signal representative of an amount of a coating discharged in the workstation;

a database for storing data values representative of the signal;

a network configured for allowing access to the database;

at least one computing device for access to the database over the network and providing a user interface for presenting information representative of at least a portion of the data values;

wherein the coating comprises a paint.

12. The system of claim 11 wherein the paint comprises a surface finish.

13. The system of claim 12 wherein the paint includes a pigment.

14. The system of claim 13 wherein the paint includes a solvent.

15. The system of claim 14 wherein the paint includes a volatile organic compound.

16. The system of claim 15 wherein the paint comprises a spray.

17. The system of claim 11 wherein the database comprises a local database and a corporate database.

18. The system of claim 17 wherein the computing device is configured to provide at least one of the data values to, the local database.

19. The system of claim 18 wherein the computing device is configured to provide at least one of the data values to the corporate database.

20. The system of claim 19 wherein the corporate database is configured to obtain the data values from the local database at predetermined intervals.

21. The system of claim 20 wherein the corporate database is configured to obtain the data values from the local database at least about every 24 hours.

22. The system of claim 21 wherein the local database and the corporate database provide referential integrity of the data values.

23. The system of claim 21 wherein the data values are arranged in the database in third normal form.

24. The system of claim 19 wherein the network comprises a local network.

25. The system of claim 19 wherein the network includes the Internet.

26. The system of claim 21 wherein the data values are representative of a parameter of the coating.

27. The system of claim 26 wherein at least one of the data values comprises the amount of the coating discharged in the workstation.

28. The system of claim 26 wherein at least one of the data values comprises an amount of time the coating is discharged in the workstation.

29. The system of claim 26 wherein at least one of the data values comprises an amount of volatile organic compounds of the coating.

30. The system of claim 26 wherein at least one of the data values comprises at least one of color information and batch information relating to the coating.

31. The system of claim 19 wherein the sensor comprises a detector.

32. The system of claim 19 wherein the sensor is coupled to a computing device.

33. The system of claim 19 wherein the sensor comprises a flow meter.

34. The system of claim 19 wherein the computing device comprises at least one of a personal digital assistant, a personal computer, a microcomputer, a digital device, and a programmable logic controller.

35. The system of claim 19 wherein the computing device comprises a computer.

36. The system of claim 19 wherein the computing device is configured to access the data values in substantially real time.

37. The system of claim 19 wherein the computing device is configured to provide a report.

38. A system for monitoring the emission of volatile organic compounds in a workstation comprising:

a sensor to obtain a signal representative of an amount of a coating discharged in the workstation;

a database for storing data values representative of the signal;

a network configured for allowing access to the database;

at least one computing device for access to the database over the network and providing a user interface for presenting information representative of at least a portion of the data values;

wherein at least a portion of the data values are representative of a parameter of the coating, and wherein at least one of the data values comprises: (a) the amount of the coating discharged in the workstation; (b) an amount of time the coating is discharged in the workstation; (c) an amount of volatile organic compound content of the coating; and (d) at least one of color information and batch information relating to the coating.

39. The system of claim 38 wherein the color information comprises a color of the coating.

40. The system of claim 39 wherein the batch information comprises a batch of the coating.

41. The system of claim 40 wherein the coating comprises a paint.

42. The system of claim 38 wherein the coating comprises a surface finish.

43. The system of claim 41 wherein the coating includes a pigment.

44. The system of claim 43 wherein the coating includes a solvent.

45. The system of claim 44 wherein the coating includes a volatile organic compound.

46. The system of claim 45 wherein the coating comprises a spray.

47. The system of claim 41 wherein the database comprises a local database and a corporate database.

48. The system of claim 47 wherein the computing device is configured to provide at least one of the data values to the local database.

49. The system of claim 48 wherein the computing device is configured to provide at least one of the data values to the corporate database.

50. The system of claim 49 wherein the corporate database is configured to obtain the data values from the local database at predetermined intervals.

51. The system of claim 50 wherein the corporate database is configured to obtain the data values from the local database at least about every 24 hours.

52. The system of claim 51 wherein the local database and the corporate database provide referential integrity of the data values.

53. The system of claim 51 wherein the data values are arranged in the database in third normal form.

54. The system of claim 49 wherein the network comprises a local network.

55. The system of claim 49 wherein the network includes the Internet.

56. The system of claim 49 wherein the sensor comprises a detector.

57. The system of claim 49 wherein the sensor is coupled to a computing device.

58. The system of claim 49 wherein the sensor comprises a flow meter.

59. The system of claim 49 wherein the computing device comprises at least one of a personal digital assistant, a personal computer, a microcomputer, a digital device, and a programmable logic controller.

60. The system of claim 49 wherein the computing device comprises a computer.

61. The system of claim 49 wherein the computing device is configured to access the data values in substantially real time.

62. The system of claim 49 wherein the computing device is configured to provide a report.

63. A system for monitoring the emission of volatile organic compounds in a workstation comprising:
- a sensor configured to obtain a signal representative of an amount of a coating discharged in the workstation;
- a database for storing data values representative of the signal;
- a network configured for allowing access to the database;
- at least one computing device for access to the database over the network and providing a user interface for presenting information representative of at least a portion of the data values;
- wherein the coating comprises a finish.

64. The system of claim 63 wherein the finish comprises a paint.

65. The system of claim 64 wherein the finish includes a pigment.

66. The system of claim 65 wherein the finish includes a solvent.

67. The system of claim 66 wherein the finish includes a volatile organic compound.

68. The system of claim 67 wherein the finish comprises a spray.

69. The system of claim 63 wherein the database comprises a local database and a corporate database.

70. The system of claim 69 wherein the computing device is configured to provide at least one of the data values to the local database.

71. The system of claim 70 wherein the computing device is configured to provide at least one of the data values to the corporate database.

72. The system of claim 71 wherein the corporate database is configured to obtain the data values from the local database at predetermined intervals.

73. The system of claim 72 wherein the corporate database is configured to obtain the data values from the local database at least about every 24 hours.

74. The system of claim 73 wherein the local database and the corporate database provide referential integrity of the data values.

75. The system of claim 73 wherein the data values are arranged in the database in third normal form.

76. The system of claim 71 wherein the network comprises a local network.

77. The system of claim 71 wherein the network includes the Internet.

78. The system of claim 73 wherein the data values are representative of a parameter of the coating.

79. The system of claim 78 wherein at least one of the data values comprises the amount of the coating discharged in the workstation.

80. The system of claim 78 wherein at least one of the data values comprises an amount of time the coating is discharged in the workstation.

81. The system of claim 78 wherein at least one of the data values comprises an amount of volatile organic compounds of the coating.

82. The system of claim 78 wherein at least one of the data values comprises at least one of color information and batch information relating to the coating.

83. The system of claim 71 wherein the sensor comprises a detector.

84. The system of claim 71 wherein the sensor is coupled to a computing device.

85. The system of claim 71 wherein the sensor comprises a flow meter.

86. The system of claim 71 wherein the computing device comprises at least one of a personal digital assistant, a personal computer, a microcomputer, a digital device, and a programmable logic controller.

87. The system of claim 71 wherein the computing device comprises a computer.

88. The system of claim 71 wherein the computing device is configured to access the data values in substantially real time.

89. The system of claim 71 wherein the computing device is configured to provide a report.

* * * * *